United States Patent
Barber et al.

(10) Patent No.: US 10,720,229 B2
(45) Date of Patent: Jul. 21, 2020

(54) REDUCING ERROR IN PREDICTED GENETIC RELATIONSHIPS

(71) Applicant: Ancestry.com DNA, LLC, Lehi, UT (US)

(72) Inventors: Mathew J Barber, Chicago, IL (US); Yong Wang, Foster City, CA (US); Keith D. Noto, San Francisco, CA (US); Kenneth G. Chahine, Park City, UT (US); Catherine Ann Ball, Mountain View, CA (US)

(73) Assignee: Ancestry.com DNA, LLC, Lehi, UT (US)

( * ) Notice: Subject to any disclaimer, the term of this patent is extended or adjusted under 35 U.S.C. 154(b) by 492 days.

(21) Appl. No.: 15/519,104

(22) PCT Filed: Oct. 14, 2015

(86) PCT No.: PCT/US2015/055579
§ 371 (c)(1),
(2) Date: Apr. 13, 2017

(87) PCT Pub. No.: WO2016/061260
PCT Pub. Date: Apr. 21, 2016

(65) Prior Publication Data
US 2017/0220738 A1   Aug. 3, 2017

Related U.S. Application Data

(60) Provisional application No. 62/063,849, filed on Oct. 14, 2014.

(51) Int. Cl.
*G16B 40/00*   (2019.01)
*G16B 10/00*   (2019.01)
(Continued)

(52) U.S. Cl.
CPC ............. *G16B 40/00* (2019.02); *G06N 5/048* (2013.01); *G06N 7/005* (2013.01); *G16B 10/00* (2019.02); *C12Q 1/6881* (2013.01); *G16B 20/40* (2019.02)

(58) Field of Classification Search
CPC ............. C12Q 2600/156; C12Q 1/6883; C12Q 2600/172; G16B 20/00; G16B 40/00;
(Continued)

(56) References Cited

U.S. PATENT DOCUMENTS

2010/0223281 A1   9/2010   Hon et al.
2012/0053845 A1   3/2012   Bruestle et al.
(Continued)

OTHER PUBLICATIONS

Browning, S.R. et al., "Identity by Descent Between Distant Relatives: Detection and Applications," Annu. Rev. Genet., 2012, vol. 46, pp. 617-633.

(Continued)

*Primary Examiner* — Mary K Zeman
(74) *Attorney, Agent, or Firm* — Fenwick & West LLP

(57) ABSTRACT

System, computer program products, and methods are disclosed for estimating a degree of ancestral relatedness between two individuals. The haplotype data for a population of individuals is divided into segment windows based on genetic markers, and matched segments for the haplotype data are generated. Each matched segment having a first cM width that exceeds a threshold cM width is included in counting the matched segments in each segment window. A weight associated with each segment window is estimated based on the count of matched segments in the associated segment window. A weighted sum of per-window cM widths for each matched segment is calculated based on the first cM width and the weights associated with the segment windows of the matched segment. The weighted sum of per-window cM widths are used to estimate a degree of ancestral relatedness between two individuals.

20 Claims, 11 Drawing Sheets

(51) Int. Cl.
*G06N 5/04* (2006.01)
*G06N 7/00* (2006.01)
*C12Q 1/6881* (2018.01)
*G16B 20/40* (2019.01)

(58) Field of Classification Search
CPC ........ G16B 45/00; G16B 50/00; G16B 10/00; G16B 20/20; G16B 20/40; G16B 30/00; G16B 5/00; G06Q 50/22; G16H 10/60; G06F 16/288; G06N 3/02; G06N 5/048; G06N 7/005
See application file for complete search history.

(56) References Cited

U.S. PATENT DOCUMENTS

| | | | |
|---|---|---|---|
| 2014/0025308 A1* | 1/2014 | Jorde | G16B 30/00 702/19 |
| 2014/0067355 A1 | 3/2014 | Noto et al. | |
| 2014/0278138 A1 | 9/2014 | Barber et al. | |
| 2017/0213127 A1* | 7/2017 | Duncan | G16B 50/00 |
| 2018/0044730 A1* | 2/2018 | Pickrell | C12Q 1/6874 |
| 2019/0205502 A1* | 7/2019 | Staples | G06F 16/288 |

OTHER PUBLICATIONS

Browning, S.R. et al., "Rapid and Accurate Haplotype Phasing and Missing-Data Inference for Whole-Genome Association Studies by Use of Localized Haplotype Clustering," The American Journal of Human Genetics, Nov. 2007, vol. 81, pp. 1084-1096.

European Extended Search Report, European Application No. 15850218.7, dated Mar. 5, 2018, 5 pages.

Gusev, A. et al., "The Architecture of Long-Range Haplotypes Shared Within and Across Populations," Mol. Biol. Evol., 2012, vol. 29, No. 2, pp. 473-486.

Gusev, A. et al., "Whole Population, Genome-Wide Mapping of Hidden Relatedness," Genome Research, Feb. 2009, vol. 19, No. 2, pp. 318-326.

Nelder, J.A. et al., "A Simplex Algorithm for Function Minimization," The Computer Journal, Apr. 1964-Jan. 1965, vol. 7, pp. 308-313.

Padhukasahasram, B., "Inferring Ancestry from Population Genomic Data and Its Applications," Frontiers in Genetics, Jul. 3, 2014, vol. 5, pp. 1-5.

Purcell, S. et al., "Plink: a tool set for whole-genome association and population-based linkage analyses," The American Journal of Human Genetics, 2007, vol. 81, No. 3, pp. 559-575.

Sabeti, P.C. et al., "Genome-wide detection and characterization of positive selection in human populations," Nature, 2007, vol. 449, No. 7164, pp. 1-16.

The International Hapmap Consorium, "A second generation human haplotype map of over 3.1 million SNPs," Nature, 2007, vol. 449, No. 164, pp. 1-30.

PCT International Search Report & Written Opinion, International Application No. PCT/US2015/055579, dated Jan. 4, 2016, 10 Pages.

Henn, B.M., et al., "Cryptic Distant Relatives Are Common in Both Isolated and Cosmopolitan Genetic Samples," PLoS One, 2012, vol. 7, No. e34267 (14 pages).

* cited by examiner

100

```
┌─────────────────────────────────────────────────────────────────┐
│ Receive haplotype data for a population of individuals, the     │
│ haplotype data including a plurality of genetic markers shared  │
│ among the individuals                                           │
│                              102                                │
└─────────────────────────────────────────────────────────────────┘
                                  ↓
┌─────────────────────────────────────────────────────────────────┐
│ Divide the haplotype data into segment windows based on the     │
│ genetic markers                                                 │
│                              104                                │
└─────────────────────────────────────────────────────────────────┘
                                  ↓
┌─────────────────────────────────────────────────────────────────┐
│ For each individual in the population:                          │
│  ┌───────────────────────────────────────────────────────────┐  │
│  │ Based on the genetic markers,                             │  │
│  │ match segments of the haplotype data that are identical   │  │
│  │ between the individual and any other individual in the    │  │
│  │ population,                                               │  │
│  │ each matched segment having a first cM width exceeding    │  │
│  │ a threshold cM width and being part of one or more of the │  │
│  │ segment windows                                           │  │
│  │                         106                               │  │
│  └───────────────────────────────────────────────────────────┘  │
│                                ↓                                │
│  ┌───────────────────────────────────────────────────────────┐  │
│  │ Count the matched segments                                │  │
│  │ in each segment window                                    │  │
│  │                         108                               │  │
│  └───────────────────────────────────────────────────────────┘  │
│                                ↓                                │
│  ┌───────────────────────────────────────────────────────────┐  │
│  │ Estimate a weight associated with each segment window     │  │
│  │ based on the count of matched segments in the             │  │
│  │ associated segment window                                 │  │
│  │                         110                               │  │
│  └───────────────────────────────────────────────────────────┘  │
│                                ↓                                │
│  ┌───────────────────────────────────────────────────────────┐  │
│  │ Calculate a weighted sum of per-window cM widths          │  │
│  │ for each matched segment                                  │  │
│  │ based on the first cM width and the weights               │  │
│  │ associated with the segment windows of the matched segment│  │
│  │                         112                               │  │
│  └───────────────────────────────────────────────────────────┘  │
└─────────────────────────────────────────────────────────────────┘
                                  ↓
┌─────────────────────────────────────────────────────────────────┐
│ Estimate a degree of ancestral relatedness between two          │
│ individuals based on the weighted sum of per-window cM widths   │
│ of each matched segment between the two individuals             │
│                              114                                │
└─────────────────────────────────────────────────────────────────┘
```

FIG. 1A

REDUCING ERROR IN PREDICTED GENETIC RELATIONSHIPS

CROSS REFERENCE TO RELATED APPLICATIONS

The application claims the benefit of U.S. Provisional Application No. 62/063,849, filed on Oct. 14, 2014, the contents of which are incorporated herein by reference.

BACKGROUND

1. Field

The disclosed embodiments relate to computer program products, systems, and methods used to identify individuals in a population who are ancestrally related based on the individuals' genetic data.

2. Description of the Related Art

Although humans are, genetically speaking, almost entirely identical, small differences in our DNA are responsible for much of the variation between individuals. Stretches of DNA that are determined to be relevant for some purpose are referred to as haplotypes. Haplotypes are identified based on consecutive single nucleotide polymorphisms (SNPs) of varying length. Certain haplotypes shared by individuals suggests a familial relationship between those individuals based on a principal known as identity-by-descent (IBD).

Because identifying segments of IBD DNA between pairs of genotyped individuals is useful in many applications, numerous methods have been developed to perform IBD analysis (Purcell et al. 2007, Gusev A. et al., The Architecture of Long-Range Haplotypes Shared within and across Populations, *Mol. Biol. Evol.*, 29(2):473-86, 2012; Browning S. R. and Browning B. L. Rapid and accurate haplotype phasing and missing-data inference for whole-genome association studies by use of localized haplotype clustering, *American Journal of Human Genetics*, 91:1084-96, 2007; Browning S. R. and Browning B. L., Identity by descent between distant relatives: detection and applications, *Annu. Rev. Genet.*, 46:617-33, 2012). However, these approaches do not scale for continuously growing very large datasets. For example, the existing GERMLINE implementation is designed to take a single input file containing all individuals to be compared against one another. While appropriate for the case in which all samples are genotyped and analyzed simultaneously, this approach is not practical when samples are collected incrementally. The program suite GERMLINE (Gusev A. et al., Whole population, genome-wide mapping of hidden relatedness, *Genome Res.*, 19:318-26, 2009) offers an "ibs filter", which removes highly frequent matches (defined by chromosome, as well as the start and end position on the chromosome). Like GERMLINE's matched segment discovery approach, the "ibs filter" approach is designed to be fast, and is relatively simplistic as a consequence. The more accurate of these methods, such as Refined IBD, are much more accurate than the GERMLINE "ibs filter", but they do not scale computationally and would be difficult to integrate into an analytical pipeline even if they did. There are many existing methods that assess evidence for a matched segment not just by centimorgan width, as is done within GERMLINE. Examples include Refined IBD, fast IBD, SLRP, and PARENTE. They emphasize that differences between these approaches are a tradeoff between model complexity and computational speed (and feasibility).

SUMMARY

Methods, systems, and computer program products are disclosed for estimating a degree of ancestral relatedness between two individuals. The computer program products include TIMBER. To estimate the ancestral relatedness of two individuals methods include receiving haplotype data from a population of individuals. The haplotype data include a plurality of genetic markers that are shared among the individuals in the population. The haplotype data is then divided into segment windows based on the genetic markers. In some embodiments, the genetic markers include single nucleotide polymorphisms (SNPs) and the haplotype data is divided into K segment windows including an equal number d of SNPs. In some embodiments, the haplotype data is divided into 4105 segment windows of 96 SNPs.

For each individual, the method includes matching segments of the haplotype data that are identical between the individual and any other individual in the population, wherein the matching is based on the genetic markers. Each matched segment has a first centimorgan (cM) width that exceeds a threshold cM width. In some embodiments, the threshold cM width is 5 cM. Each matched segment is part of one or more of the segment windows. The matched segments in each segment window are then counted. The count of matched segments in a segment window is also referred to as a per-window match count.

For each individual, the method includes estimating a weight associated with each segment window based on the count of matched segments in the associated segment window. In some embodiments, the weight associated with a segment window is decreased as the count of matched segments increases. The benefit of decreasing weights for increasing per-window match counts includes reducing the effect of matched segments that are likely not from the recent genealogical history (RGH) of the individuals, but rather from a more distant common ancestry at the human, ethnicity, or sub-ethnicity level.

For each individual, the method includes calculating a weighted sum of per-window cM widths for each matched segment based on the first cM width and the weights associated with the segment windows of the matched segment. A degree of ancestral relatedness between two individuals is estimated based on the weighted sum of per-window cM widths of each matched segment between the two individuals. In some embodiments, the degree equals the weighted sum of per-window cM widths. In some embodiments, the weighted sum of per-window cM widths is the sum of the first cM widths for each segment window of a matched segment between the two individuals multiplied by the two weights for each individual associated with these segment windows.

In some embodiments, TIMBER, an ancestry prediction machine matching genetic markers, is a procedure operating on a computer for refining each individual's list of matched segments and prioritizing the matched segments that are most likely to be from the individuals' recent genealogical history. TIMBER uses the matched segments to remove the effect of "noisy" segment windows within the haplotype data that display an "excessive" count of matched segments between numerous individuals. In some embodiments, a count is excessive if the count is larger than 10 or 20. It is less likely that a matched segment is from recent genealogical history if a matched segment is mainly part of "noisy" segment windows. TIMBER estimates weights from the matched segment data and estimates a weighted sum of per-window cM widths of a matched segment based on discounting "noisy" segment windows. TIMBER is computationally efficient and scalable, allowing reevaluating an entire population of individuals each time new individuals are added to the population.

BRIEF DESCRIPTION OF THE DRAWINGS

FIG. 1A illustrates a flowchart of a method for estimating a degree of ancestral relatedness between two individuals, according to some embodiments.

Figure 1B:
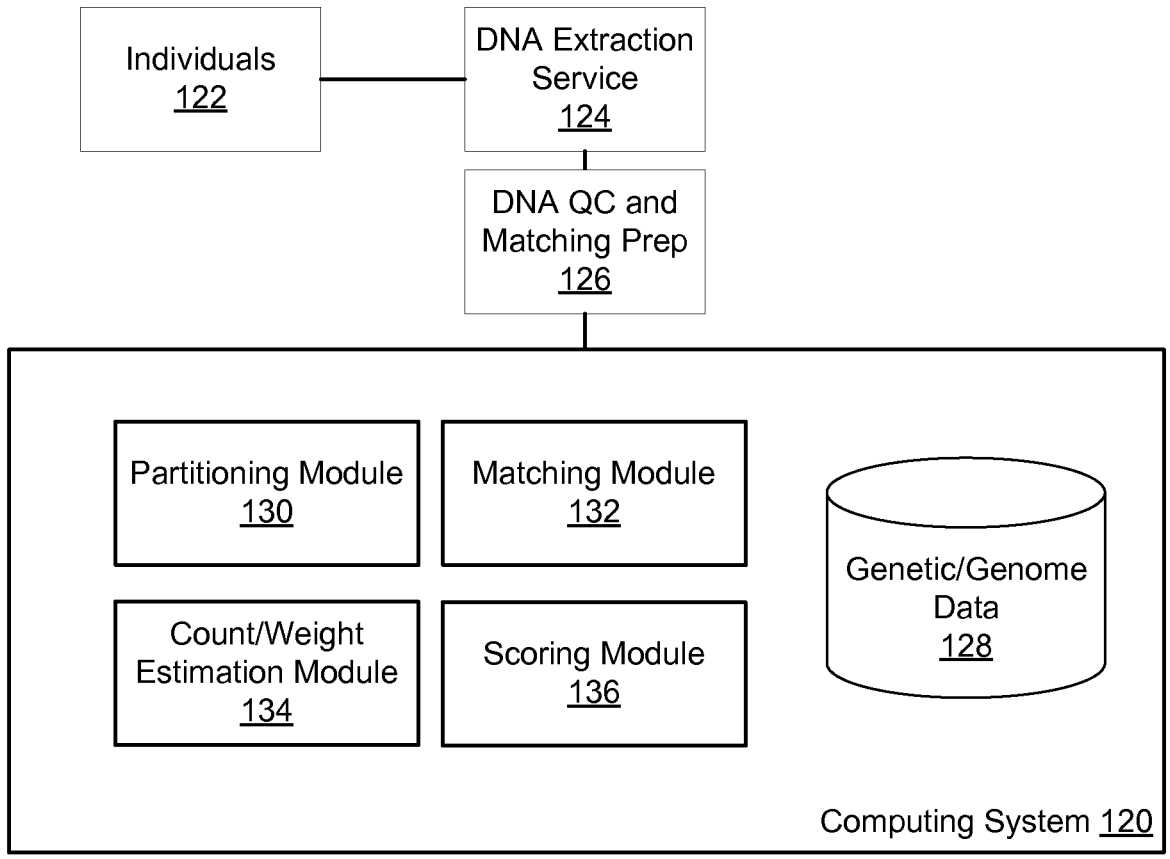
FIG. 1B is a block diagram of a computing environment for estimating a degree of ancestral relatedness between two individuals, according to one embodiment.

The figures depict an embodiment for purposes of illustration only. One skilled in the art will readily recognize from the following description that alternative embodiments of the structures and methods illustrated herein may be employed without departing from the principles described herein.

DETAILED DESCRIPTION

I. Overview

Methods, systems, and computer program products are disclosed for estimating a degree of ancestral relatedness between two individuals. Estimating the ancestral relatedness of individuals includes identifying and scoring identical-by-descent (IBD) matched segments among the haplotype data of these individuals. To identify IBD segments, the method compares genetic markers among the individuals' haplotypes. In some embodiments, genetic markers include single-nucleotide polymorphisms (SNPs). Segments from two individuals are considered identical by state (IBS) if the genetic markers along the individuals' haplotype sequences in these segments are identical at the same loci along the haplotypes. Throughout the disclosure unless otherwise stated, "matched haplotype segments" or "matched segments" refer to identical haplotype segments shared between two or more individuals. Generally, an IBS segment shared between two individuals is identical by descent (IBD) if the individuals inherited the IBS segment from a common ancestor, sharing the same ancestral origin. Thus, any IBD segment by definition also represents an IBS segment, while the reverse is typically not true, i.e., an IBS segment might not represent an IBD segment. Moreover, many IBD segments are not from the recent genealogical history (RGH) of individuals, but rather from a more distant common ancestry at the human, ethnicity, or sub-ethnicity level. The disclosed method allows for prioritizing matched segments that are more likely to be from the individuals' RGH over those segments that are from a more distant common ancestry, thus belonging to their distant ancestral past, i.e., non-recent genealogical history (non-RGH).

FIG. 1A is a flowchart illustrating a method 100 for estimating a degree of ancestral relatedness between two individuals, according to some embodiments. The method allows the user to input segments that are categorized as matched or discovered, i.e., having a first centimorgan (cM) width of over 5 cM. The method in form of the TIMBER program then uses those matched segments to calculate a weighted sum of per-window cM widths. The weighted sum of per-window cM widths takes into account the count of matched segments to other individuals of the population in the segment windows, down weighting segment windows that display a high degree of matched segments to many individuals.

In some embodiments, the inputs to TIMBER program are the pairwise matched segments between all individuals in a population stored in a database. The pairwise matched segments are translated into weights for each individual's matchable segment windows of the genome by the TIMBER program. The TIMBER program then uses the weights to re-calibrate or re-score the original pairwise matched segments.

In some embodiments, TIMBER programs, wherein the TIMBER programs are stored in memory and configured to be executed by one or more processors of a computing device, the TIMBER programs including instructions when executed by the computing device cause the device to:
1. calculate the counts of matched segments in each segment window of the haplotype data, for each individual of the population, where the matched segments are between the individual and every other person in the database,
2. calculate weights for each individual and segment window, and
3. calculate a weighted sum of per-window cM widths for each matched segment between two individuals based on the weights.

The method 100 is performed at a computing device, such as the computing device, as may be controlled by specially programmed code (computer programming instructions) contained, for example, in the TIMBER program, wherein such specially programmed code is or is not natively present in the computing device. Embodiments of the computing device include, but are not limited, general-purpose computers, e.g., a desktop computer, a laptop computer, computing servers, tablets, mobile devices, or any similar computing devices. Once programmed to execute the methods described here, such a computing device becomes a special-purpose computer. Some embodiments of the method 100 may include fewer, additional, or different steps than those shown in FIG. 1A, and the steps may be performed in different orders. The steps of the method 100 are described with respect to example haplotype data illustrated in Figures (FIGS. 2 through 9).

FIG. 1B is a block diagram of an environment for using a computer system 120 to estimate a degree of ancestral relatedness between two individuals, according to some embodiments. Depicted in FIG. 1B are individuals 122 (i.e. a human or other organism), a DNA extraction service 124, and a DNA quality control (QC) and matching preparation service 126.

Individuals 122 provide DNA samples for analysis of their genetic data. In some embodiment, an individual uses a sample collection kit to provide a sample, e.g., saliva, from which genetic data can be reliably extracted according to conventional methods. DNA extraction service 124 receives the sample and genotypes the genetic data, for example by extracting the DNA from the sample and identifying values of SNPs present within the DNA. The result is a diploid genotype. DNA QC and matching preparation service 126 assesses data quality of the diploid genotype by checking various attributes such as genotyping call rate, genotyping heterozygosity rate, and agreement between genetic and self-reported gender. System 120 receives 102 the haplotype data from DNA extraction service 124 and optionally stores the haplotype data in a database 128 containing unphased DNA diploid genotypes, phased haplotypes, and other genomic data. Unless otherwise stated, haplotype data refers to any genetic or genome data obtained from the individuals 122, which is optionally stored in database 128.

In some embodiments, the partitioning module 130 divides 104 the haplotype data into segment windows based on the genetic markers. In some embodiments, the matching module 132 matches 106 segments of the haplotype data that are identical between the individual and any other individual in the population, where each matched segment has a first cM width that exceeds a threshold cM width and is part of one or more of the segment window.

In some embodiments, the count/weight estimation module 134 counts 108 the matched segments in each segment window and estimates 110 a weight associated with each segment window based on the count of matched segments in the associated segment window.

The scoring module 136 then calculates 112 a weighted sum of per-window cM widths for each matched segment based on the first cM width and the weights associated with the segment windows of the matched segment. In some embodiments, the scoring module 136 estimates 114 a degree of ancestral relatedness between two individuals based on the weighted sum of per-window cM widths of each matched segment between the two individuals.

II. Embodiments of the Ancestral Relationship Prediction Programs

In some embodiments, matched segments among a population of individuals are generated based on the individuals' haplotype data. In some embodiments, the matched segments are stored in a database for later retrieval by the TIMBER program. The TIMBER program is configured to receive all the matched segments among a population of individuals and prioritize those matched segments that are from the individuals' recent genealogical history (RGH).

II.A. Match Haplotype Segments

The method 100 includes receiving 102 haplotype data for a population of individuals, the haplotype data including a plurality of genetic markers shared among the individuals, according to some embodiments. In some embodiments, to identify (match) and score IBD segments among the haplotype data, the method 100 uses a HADOOP® reimplementation of a matching algorithm. The method benefits from being computationally fast and scalable for larger-sized populations. In some embodiments, the matched IBS segments based on the haplotype data of individuals include the individuals' RGH and non-RGH segments. The matched IBS segments are generally referred to as matched segments. In some embodiments, matched segments are generated using methods that are well known in the art. Using, for example, the TIMBER program, the method 100 then prioritizes the matched segments into segments that are more likely from the RGH of two individuals compared to from their non-RGH by calculating a TIMBER score that quantifies the likelihood of two individuals sharing a common recent ancestral relationship.

The method for determining the TIMBER score is based on the assumption that the locations (loci) of matched segments from an individual's RGH are evenly distributed across an individual's genome. For example, by dividing the SNPs of the chromosomes across the individuals' genome into discrete windows, the counts of the segments in a specific window on chromosome 1 are independent of the counts of the segments in a window on chromosome 14. Consequently, matches between segments of individuals in a window on chromosome 1 are therefore independent from matches to segments in the window on chromosome 14, resulting in an even distribution across all windows.

Furthermore, matched segments that do not originate from an individual's RGH exhibit spikes at certain windows of the genome while being evenly distributed across the remaining windows. In some instances, these spikes can be attributed to particular reasons for the genetic variation in these windows, e.g., at a person level or at the database level. At the person level, the spikes may result from the segments of a window displaying a high level of sequence similarity across a particular ethnicity group, while at a database level, the individuals of population in the database may not possess any SNP variations across a particular window based on how the population was selected. In particular, it is unclear whether the distribution of the counts of matched segments in a window originates from an individuals' RGH, and whether factors that confound local spikes of matching are due to unknown non-RGH reasons, which are difficult to model. To overcome the problems associated with these spikes, the method introduces weights for each window for rescoring all matched segments, in particularly, the ones that contribute to the spikes in windows. In some instances, matched segments commonly occur at short and specific location of an individual's genome while matching a very large number of other individuals, e.g., larger than 1,000 individuals.

The method 100 includes dividing 104 the haplotype data into segment windows based on the genetic markers, according to some embodiments. The haplotype data includes, but is not limited to, SNPs observed across the individual's genome. In some embodiments, the haplotype data includes the haplotype data of an individual's entire or partial genome. In some embodiments, the method 100 divides the observed SNPs into K windows of equal size d, with each window, for example, including 96 SNPs. Other examples for window sizes include 50, 60, 70, 80, 90, 100, 110, 120, 130, 140, 150 or any number that falls within the range of 50 to 500. In some embodiments, the size of each window, i.e., the number of SNPs per window varies for across the windows.

For example, some windows may include only 50 SNPs depending on the sequence length of these SNPs, while other windows include 96 SNPs. In some embodiments, the windows include other genetic markers besides SNPs that are used to identify matched segments. These markers include, but are not limited to, restriction fragment length polymorphisms, simple sequence length polymorphisms, amplified fragment length polymorphism, random amplification of polymorphic DNA, variable number tandem repeat, simple sequence repeat microsatellite polymorphism, short tandem repeats, single feature polymorphisms, restriction site associated DNA markers, and the like.

In some embodiments, the method 100 includes using phased haplotype data, i.e. data for which the phase has been estimated, as input to identify matched segments. For this, the method uses the haplotype data for a population of n individuals. In some embodiments, the input of the haplotype data is represented as a 2n×s matrix H with rows corresponding to 2n haplotypes and columns to s SNPs. By vertically slicing H into non-overlapping, equal width submatrices $H_i$ of d columns, each submatrix $H_i$ then represents a different segment window i, where i=0 . . . K and s=d·K. In some embodiments, the haplotype data includes n implicit non-phased haplotypes of the population using the population's genotypes to determine possible haplotype matches without explicit haplotype matching that would require the phase of the haplotypes to be known. Haplotype matching therefore refers to implied as well as explicit haplotype matching, where the former is based on non-phased genomic data of a population.

The method 100 includes for each individual in the population, based on the genetic markers, matching 106 segments of the haplotype data that are identical between the individual and any other individual in the population, according to some embodiments. In some embodiments, the Each matched segment has a first cM width that exceeds a threshold cM width and is part of one or more of the segment windows. The matching 104 includes identifying segment windows of exact haplotype matching between two individuals in the population. Windows of exact haplotype matching are used to anchor the identifying the entire matched segment that in some instances extends beyond the initial exact window match. In some embodiments, the method 100 includes extending the exact window match until two homozygous mismatching SNPs are observed on either side of the original exact window match. As a result, the method 100 determines the segment width by determining the minimum and maximum of the start and end locations of the windows with no homozygous mismatches and extending the exact window match.

In case that the determined segment width exceeds a threshold cM width threshold width, the method 100 identifies the corresponding segment as a matched segment. In some embodiments, the threshold cM width is 5 cM. In some embodiments, the threshold cM width threshold is 6, 7, 8, 9, 10, 11, 12, 13, 14, 15 cM or any value larger than 5 cM. In some embodiments, the method 100 matches 104 segments of individuals included in a database of individuals that includes the haplotype data of each individual's genome.

II.B. Per-Window Match Count of Matched Segments

The method 100 includes for each individual in the population counting 108 the matched segments in each segment window, according to some embodiments. For each individual in the population and every window, the method 100 determines a per-window match count of matched segments. A particular per-window match count $k_1$ refers to the number of matched segments identified within the population with i indicating the window of the count. In some embodiments, since every matched segment between two individuals spans a number of windows, the method 100 translates matched segments of all individuals into the window identifiers and counts how many times each window is part of a matched segment. Matched segments of close relatives are not included in the per-window match count, which increases the likelihood that all matched segment share similar levels of uncertainty of whether or not the matched segment is part of the individuals' RGH. In some embodiments, a close relative is defined as an individual with whom the related individual has a raw TIMBER score that equals or exceeds a pre-defined close relative threshold. In some embodiments, the pre-defined close relative threshold is 50 cM. In some embodiments, the pre-defined close relative threshold is 30, 40, 50, 60, 70, 80, 90, 100 cM or any value from the range of 30 to 200 cM. A raw TIMBER score between two individuals is defined as the sum of the first cM widths of matched segments over all matched segments between the two individuals. The score is referred to as a "raw" score, since the cM widths used are the first cM widths that are not down-weighted.

In some embodiments, the method of determining the per-window match count for each individual includes the following steps:
1. initializing a per-window match count vector $\{k_i\}_{i=0 \ldots K}$ to zero counts (one value $k_i$ for every matching window in the genome, e.g., with K equal to 4105 windows, and each window including 96 SNP markers; and
2. for every matched segment:
    (a) skipping matched segment for close relatives and move to the next matched segment,
    (b) translating the matched segment into a vector of window indices $\{i\}$ (that the matched segment spans), and
    (c) incrementing the per-window match count vector entries $\{k_i\}$ by one for respective values of the vector of window indices $\{i\}$.
3. removing any entries from the per-window match count vector $\{k_i : k_i > 0\}_{i=0 \ldots K}$ having a matched segment count of zero.

Figure 2:
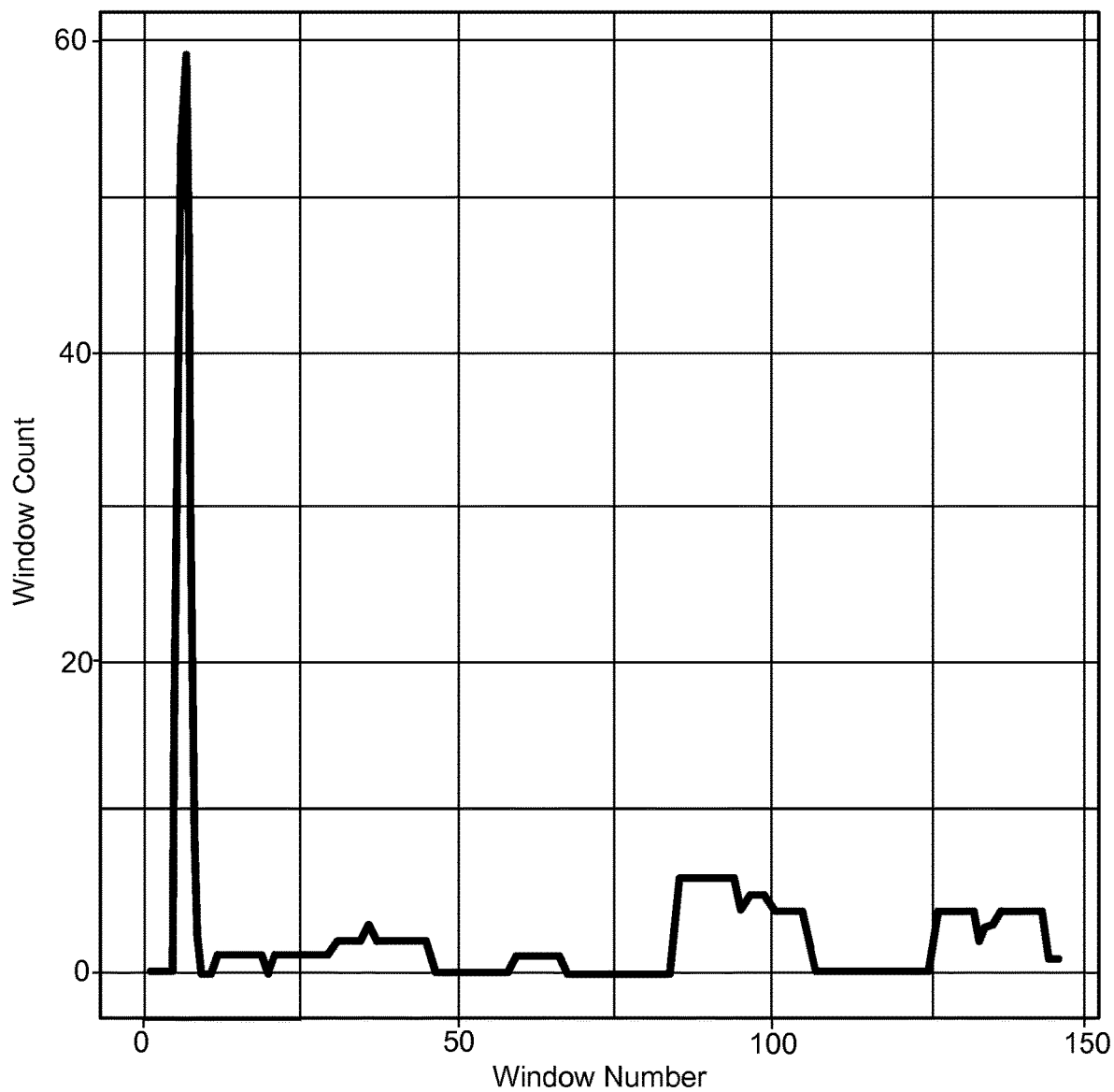
FIG. 2 illustrates an example of per-window match counts on a chunk of the genome for one individual, according to some embodiments.

FIG. 2 illustrates an example of per-window match counts on a portion of the genome of a particular individual in the population. The x-axis shows the number of a particular window i along the haplotype sequence, and the y-axis represents the total number of matched segments $k_i$ for a particular window i. In this example, the displayed windows range from number 1 to number 145. FIG. 2 displays windows with zero matched segments, while these windows are excluded from the per-window match count vector $\{k_i : k_i > 0\}_{i=0 \ldots K}$. The largest match counts are observed for window number 1 and number 2 in this example, reaching close to 60 matched segments.

Figure 3:
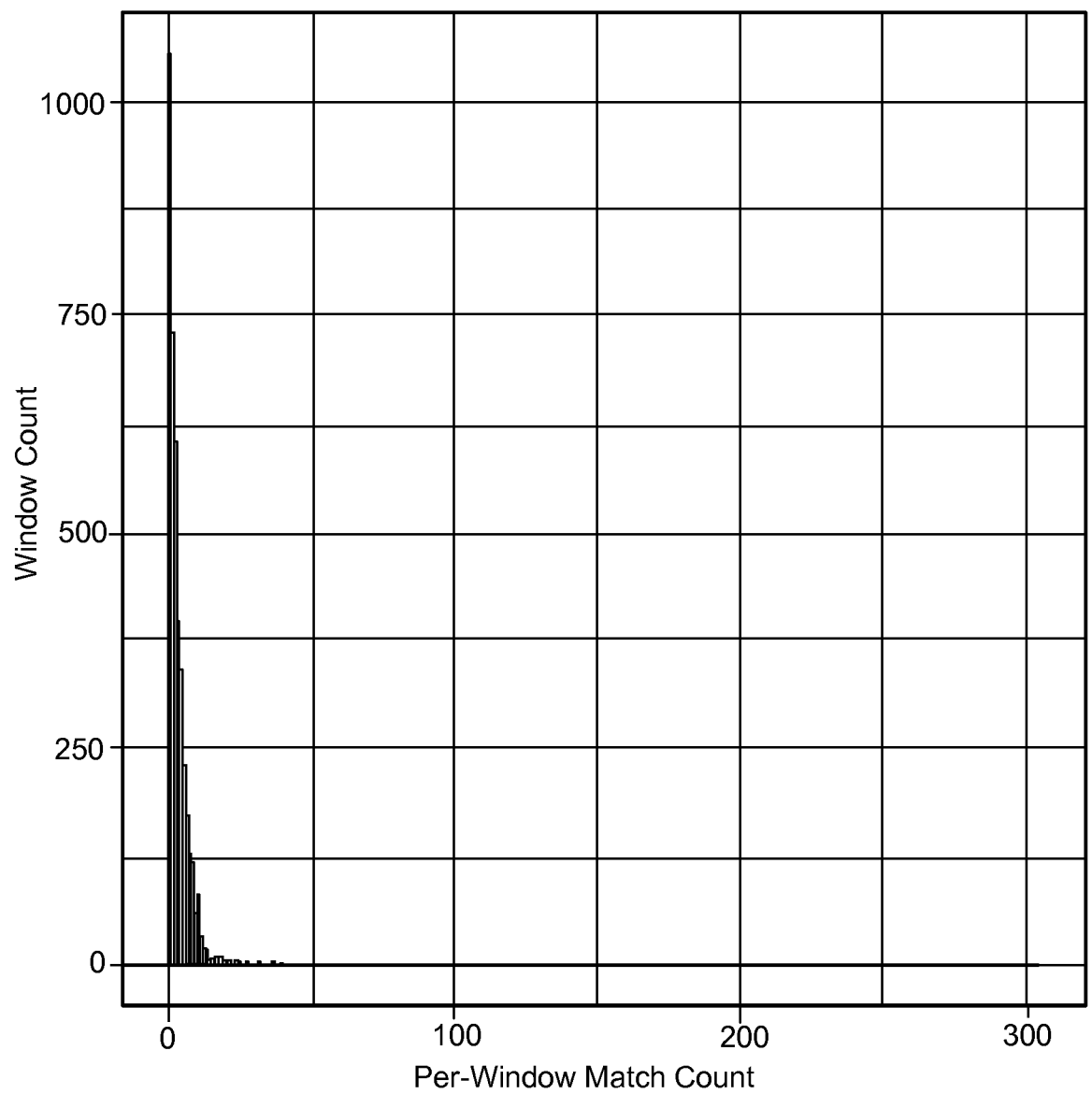
FIG. 3 illustrates an example of the histogram of per-window match counts for all of the windows in the genome for one individual, according to some embodiments.

FIG. 3 illustrates an example of the histogram of the per-window match counts $\{c : c=0 \ldots C_{max}, C_{max} \leq n\}$ for all the windows in the entire genome for an individual, which only shows a portion of the individual's genome. The histogram indicates the frequency of observing matched segments against the entire population n in each genomic window, wherein n therefore limits the maximal count per window $C_{max}$. Only windows including less than 305 matched segments are displayed with the count of windows rapidly decreasing for increasing per-window match count values. In this example, windows including zero matched segments are not shown, since these windows are not further analyzed in the method 100 of calculating the TIMBER score.

As shown in FIG. 2, certain segment windows or regions within the individual's genome display a very large count of matched segment, whether due to a high level of non-RGH matched segments for unknown reason or due to truly high distribution of matched RGH segments in these windows. The method 100 attempts to differentiate between these two possibilities by evaluating the per-window match count for every individual in the population. Furthermore, the method 100 determines a TIMBER score for each matched segment by down weighting matching windows of a matched segment that have a decreased likelihood to originate from the RGH between the two matched individuals. This down weighting, in some embodiments, includes determining a weight for each individual for a matched segment in a window.

II.C. Estimating Weights $\{w_i^A\}$

In some embodiments, the method 100 includes estimating 110 a weight associated with each segment window based on the count of matched segments in the associated segment window, according to some embodiments. In some embodiments, the estimating 110 includes determining for each individual in the population a weight for each window that counts at least one matched segment. In some embodiments, the weight is approximated by the probability that matching in that window for that individual provides evidence for RGH. This probability is related to the count of matched segments in a window. A window with an extremely high matched segment count for an individual is very unlikely due to the RGH that the individual shares with other individuals in the population. Unknown factors other than RGH may account for a very high matched segment count as described above.

To estimate the weights, the method 100 determines the probability of RGH, Prob(RGH|C=c), given the measured count c of matched segments in a window. The random variable C represents all possible counts of matched segments in a window and is assumed to be the identical across all windows. By measuring the actual counts c in particular windows, the method 100 determines the probability of RGH on the condition that C equals c for this window. To determine Prob(RGH|C=c), the method 100 uses Bayes theorem that provides:

$$Prob(RGH \mid C = c) = \frac{Prob(C = c \mid RGH)Prob(RGH)}{Prob(C = c)}, \quad (1)$$

where Prob (C=c|RGH) is the probability of having c matched segments in the window and all matched segments are due to the individuals' RGH, Prob (C=c) is the probability of having c matched segments in the window regardless of the matched segment being from RGH or non-RGH, and Prob (RGH) is the probability that the matched segment is from the individuals' RGH. Based on the Bayes theorem, the method 100 determines estimates of Prob(C=c|RGH), Prob (RGH), and Prob (C=c), wherein Prob ($\widehat{C=c}$ |RGH), Pro$\widehat{b(RGH)}$, Prob($\widehat{C}$ =c) are the estimates of Prob (C=c|RGH), Prob(RGH) and Prob(C=c), respectively. The method 100 then determines the weight $w_i^A$ for an individual A in a specific window i according to:

$$w_i^A = \frac{Prob(\widehat{C = k_i} \mid RGH)Prob\widehat{(RGH)}}{Prob(\widehat{C} = k_i)}. \quad (2)$$

In some embodiments, since it is difficult to estimate Prob(C=c|RGH), the method 100 generates at least two slightly different estimates of Prob(C=c|RGH), and then selecting the estimate of the at least two estimates that results in the greatest down weighting of C for determining the weight $w_i^A$.

II.C.1. Determine Prob($\widehat{C}$ =c) Estimate

Figure 4:
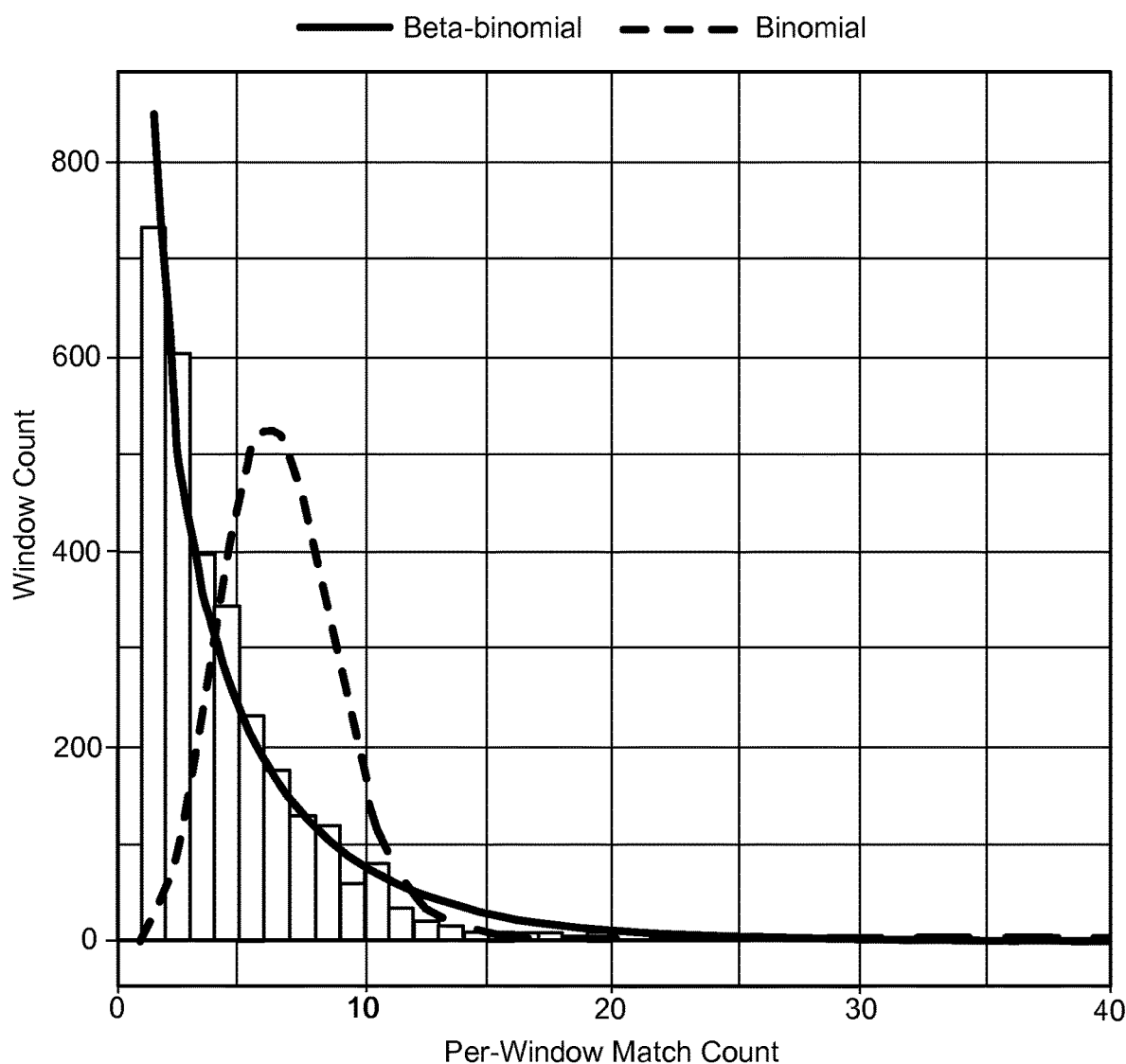
FIG. 4 is an example of the histogram of per-window match count for all the non-zero count windows where the maximum viewable per-window count is 40, according to some embodiments.

In some embodiments, the method 100 includes determining an estimate of the probability distribution of C, Prob ($\widehat{C}$ =c), which provides the likelihood that a window has a given matched segment count c for all the possible counts. These embodiments provide a more accurate prediction of the probability in the number of people that an individual matches in one window based on the probability of matching each individual in the population. For example, the value of Prob($\widehat{C}$ =20) is the probability of counting 20 matched segment in a given window for the entire haplotype data, including all matched segment of the population. Prob ($\widehat{C}$ =c) includes contributions from matched segments that are from RGH and non-RGH of the population's individuals. FIG. 4 illustrates Prob($\widehat{C}$ =c) of one individual of the population based on the individual's entire genome. Given Prob($\widehat{C}$ =c) and Prob (C=c|RGH), the method 100 is able to quantify the likelihood that a window convey information about RGH for a given count c. In some embodiments, both distributions estimate distribution of counts for counts that are greater than zero, i.e. windows that have at least one matched segment within them.

FIGS. 3 and 4 illustrate Prob($\widehat{C}$ =c) in form of a histogram of per-window match counts for all non-zero count windows without counting any windows that include zero segments. In some embodiments, only windows with zero segments are counted for at least the following two reasons: 1) different biological or observational process are the likely cause for discovering a matched segment within a window as compared to the number of discovered matched segments within that window for a given population; and 2) the weighing of windows should be based on matched segments that are actually present in and not missing from a population. Thus, these embodiments avoid effectively assigning a weight of one to windows with zero discovered matched segments. In comparison, FIG. 2 illustrates values of the counts for a specific window (and not the frequency with which that count is observed across all the non-zero windows).

To determine a distribution to the likelihood that a particular count is observed in a window, i.e., Prob(C=c), the method 100 fits a distribution of observed counts in all the non-zero windows illustrated as a histogram in FIG. 4.

In some embodiments, the method 100 uses a first beta-binomial distribution to approximate the distribution of the per-window counts, Prob($\widehat{C}$ =c), which represents the probability that each individual matches another individual in the population. The advantage of using a beta-binomial distribution is that it is able to account for the underlying heterogeneity in the probability of matching individuals without identifying the reason for the heterogeneity. As illustrated in FIG. 4, the beta-binomial distribution provides a good fit to per-window counts in an individual. In comparison, if all individuals in the population are assumed to match with an equal chance to any other individuals in the population, the binomial distribution provides a model of the observed counts in all the non-zero windows. A binomial distribution would typically be used to model the probability of a number of events being successful, if the known probability of success is shared across all the independent events.

FIG. 4 further illustrates an example of fitting a binomial distribution to the per-window counts in an individual as compared to a beta-binomial distribution. Generally, the beta-binomial distribution is preferred for modeling Prob($\widehat{C}$ =c). In particular, FIG. 4 illustrates an example of the histogram of per-window match count for all the non-zero count windows where the maximum displayed per-window match count is 40. The binominal distribution modeling Prob($\widehat{C}$ =c) is shown as a dashed line with the solid line indicating the fit of the beta-binomial distribution to the histogram data.

In some embodiments, the method 100 determines two parameters $\alpha$ and $\beta$ of the beta-binomial distribution to determine the optimal fit between the beta-binomial distribution and the per-window match count of matched segments for one individual based on the entire population of individuals. Since beta-binomial distribution is defined for counts from zero to a maximal count n that equals the population size, the method 100 uses a modified per-window match count vector that is obtained by subtracting one from each element of $\{k_i : k_i > 0\}_{i=0 \ldots K}$. The number of observations used to determine the beta-binomial distribution equals the number of windows K across the haplotype data. For example, the haplotype data is divided into 4105 windows, each window including 96 markers. The joint beta-binomial distribution $f(\{k_i\} | n, \alpha, \beta, k_i > 0)$ is given by:

$$f(\{k_i\} | n, \alpha, \beta, k_i > 0) = \prod_{i=1}^{K} \binom{n}{k_i - 1} \frac{B(k_i - 1 + \alpha, n - k_i + 1 + \beta)}{B(\alpha, \beta)}, \quad (3)$$

where $\{k_i : k_i > 0\}_{i=0 \ldots K}$ is the vector of per-window counts (for the K windows with at least one matched segment), n is the population size, $\alpha$ and $\beta$ are parameters of the distribution, and B is the beta function. Prob(C=c) for a population size n is then given by:

$$Prob(C = c | c > 0) = \binom{n}{c} \frac{B(c + \alpha, n - c + \beta)}{B(\alpha, \beta)}. \quad (4)$$

The method 100 uses the haplotype data of all individuals who match an individual to determine the parameters $\alpha$ and $\beta$ of the distribution associated with this individual. This determination is based in part on the assumption that count of each window is independent from the count of any other window. For typical examples, this assumption provides a good estimation of actual data. In some instances, this assumption might not hold true, and other distribution functions can provide better approximations to the data.

In some embodiments, the method 100 uses maximum-likelihood estimation to determine the two parameters $\alpha$ and $\beta$ of the joint beta-binomial distribution $f(\{k_i\} | n, \alpha, \beta)$ The observed per-window match count vector $\{k_i : k_i > 0\}_{i=0 \ldots K}$ represents at most K fixed parameters of the likelihood function, $\mathcal{L}(\alpha, \beta | \{k_i\}, n) = f(\{k_i\} | n, \alpha, \beta)$. The parameters $\alpha$ and $\beta$ are real numbers larger than zero that maximize the average logarithm of the likelihood function.

In some embodiments, the method 100 uses an optimization method 100 for estimating the maximum-likelihood $\mathcal{L}(\alpha, \beta | \{k_i\}, n)$ of the joint beta-binomial distribution for given $\{k_i\}$ and n. Various optimization methods are well-known in the art, each of which can be used for the maximum-likelihood estimation. In some embodiments, the method 100 applies the "Nelder-Mead" simplex optimization (Nelder J. A. and Mead R., A simplex algorithm for Function Minimization, *Computer J.*, 7:308-13, 1965) algorithm as the optimization method 100. The parameters $\alpha$ and $\beta$ are initially set to starting values denoted by $\tilde{\alpha}$ and $\tilde{\beta}$ provided by:

$$\tilde{\alpha} = \frac{nE1 - E2}{n\left(\frac{E2}{E1} - E1 - 1\right) + E1}, \quad (5)$$

$$\tilde{\beta} = \frac{(n - E1) \cdot \left(n - \frac{E2}{E1}\right)}{n\left(\frac{E2}{E1} - E1 - 1\right) + E1}, \quad (6)$$

$$\text{where } E1 = \frac{\sum_{i=1}^{K} (k_i - 1)}{n} \text{ and } E2 = \frac{\sum_{i=1}^{K} (k_i - 1)^2}{n}.$$

The parameter $\alpha$ and $\beta$ obtained by the optimization method 100 are denoted by $\hat{\alpha}$ and $\hat{\beta}$. All individuals thus have an estimated beta-binomial distribution to describe Prob $$(C = c | c > 0) = \binom{n}{c} \frac{B(c + \hat{\alpha}, n - c + \hat{\beta})}{B(\hat{\alpha}, \hat{\beta})},$$

where $\hat{\alpha}$ and $\hat{\beta}$ are specific to each individual in a population of size n, illustrated in the example of FIG. 4.

II.C.2. Determine Prob($\widehat{C = c}$ |RGH) Estimates

In some embodiments, the method 100 determines an estimate of the probability distribution Prob($\widehat{C = c}$ |RGH) by fitting a second beta-binomial distribution to the per-window match counts that only include windows with a low match count while excluding windows with a higher match count. The first beta-binomial distribution is based on the fit to Prob($\widehat{C = c}$), as described above.

In some embodiments, the method 100 excludes any per-window match counts that exceed a threshold value V. Excluding windows with higher match counts is based on the rationale that windows with low match count are mainly due to matched segments from the individuals' RGHs, while high match count windows likely include matched segment that are a mixture of RGH and non-RGH. Generally, Prob($\widehat{C = c}$ |RGH) can be estimated from Prob (C=c), as the later distribution represents the sum of two conditional distributions Prob(C=c|RGH) and Prob (C=c|non-RGH).

However, neither of these conditional distributions are known with any confidence or can be easily determined from Prob(C=c), in part because one cannot distinguish between matched segments that are from the individuals' RGHs and matched segments that are not. Attempts in estimating Prob($\widehat{C=c}$ |RGH) directly from Prob(C=c) therefore result often in poor and sometimes very poor estimates, while adding various computational problems.

Furthermore, Prob(C=c) is well estimated by a beta-binomial distribution as described above. To estimate Prob(C=c|RGH), the method 100 therefore fits a second beta-binomial distribution to the per-window match counts based on windows having a match count below or equal to the threshold value V.

Figure 5:
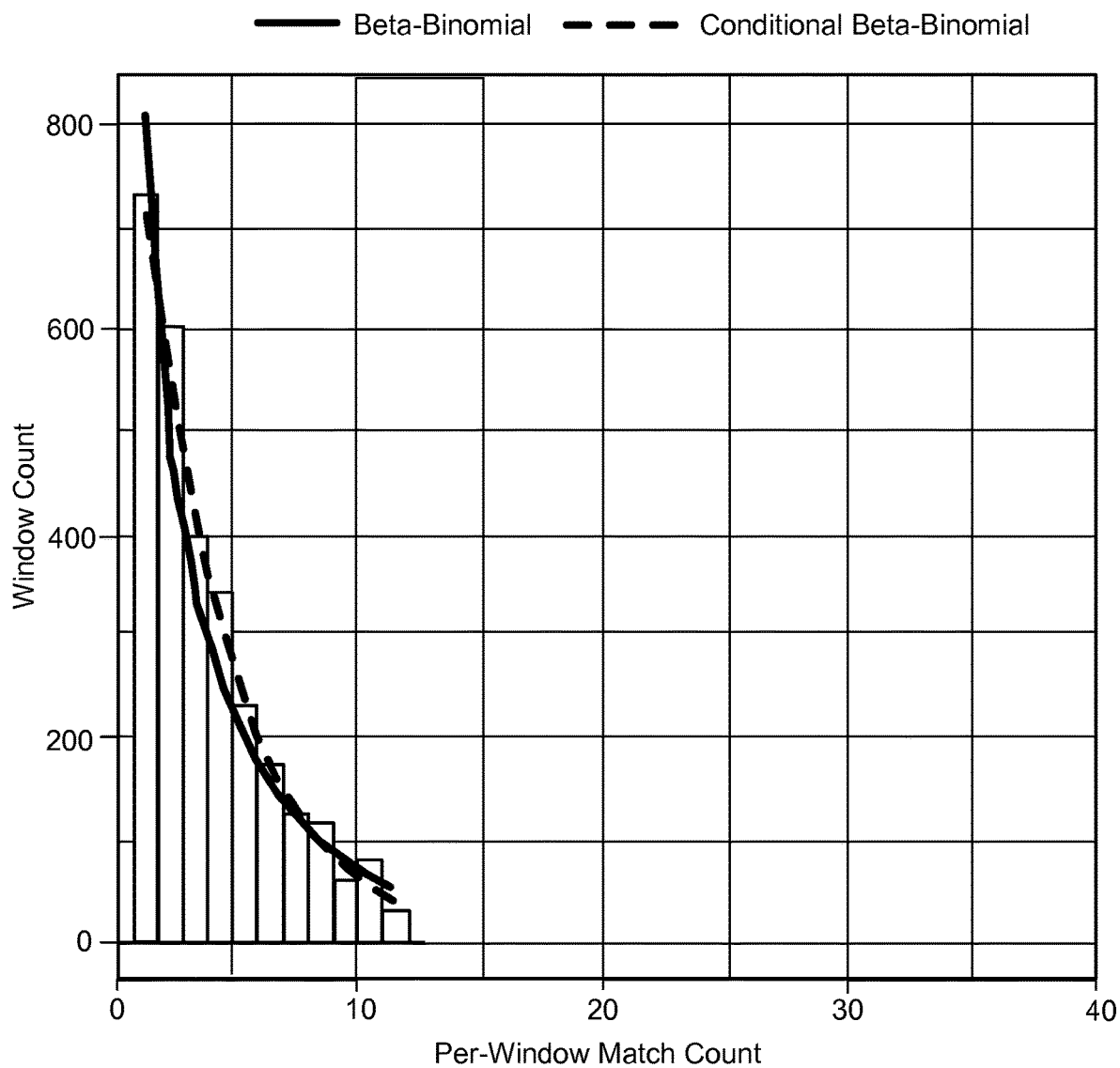
FIG. 5 is an example of the histogram of per-window match counts for all the non-zero and also low match count windows, according to some embodiments.

As illustrated in FIG. 5, both fitted distributions of Prob(C=c) and Prob(C=c|RGH) are similar to each other, if the distribution of counts for the high value windows that are not included in the fit of Prob($\widehat{C=c}$ |RGH) is consistent with the distribution estimated from only the low match count windows. FIG. 5 shows the first beta-binomial distribution based on all the non-zero count windows (shown by the solid line), the second beta-binomial distribution based on only the low match count windows (shown by the dashed line), and the histogram based only on the data from the low match count windows. The maximum displayed per-window match count is 40.

In some embodiments, since the estimate Prob($\widehat{C=c}$ |RGH) is likely sensitive to the user-specified threshold value V, the method 100 determines at least two estimates of Prob (C=c|RGH, V) using at least two different values of V. The method 100 then selects the estimate that results in smaller weights for the windows, more effectively down-weighting the individuals' matched segment counts as described in more detail below. In some embodiments, the method 100 determines only one estimate of Prob($\widehat{C=c}$ |RGH). In some embodiments, V is specified as the maximum value of a minimum threshold value $V_{min}$ and a quantile of all the counts in windows with at least one matched segment. In some embodiments, the minimum threshold value $V_{min}$ is set to 11. In some embodiments, the minimum threshold value $V_{min}$ is 1, 2, 3, 4, 5, 6, 7, 8, 9, 10, 12, 13, 14, 15, 20, 25, 30, or larger than 30. In some embodiments, at least two quantiles are specified to determine the at least two estimates of Prob ($\widehat{C=c}$ |RGH,V). In some embodiments, two specified quantiles are 75% and 90%, respectively. In some embodiments, the first specified quantile equals to 50%, 55%, 60%, 65%, or 70%, and the second specified quantile equals to 65%, 70%, 75%, 80%, or 85%. In some embodiments, the two quantiles are specified so that the difference between the two quantiles is in the range of 10%-20%, and the smaller quantile equals to 50%, 55%, 60%, 65%, 70%, 75% or any value in the range of 40%-80%.

In some embodiments, to estimate Prob(C=c|RGH, V) the method 100 uses a joint beta-binomial distribution $f(\{m_i\}|n, \alpha, \beta, V, m_i>0)$ that depends on V, $\alpha$ and $\beta$ and is given by:

$$f(\{m_i\}|n, \alpha, \beta, V, m_i > 0) = \frac{\prod_{i=1}^{M} \binom{n}{m_i - 1} \frac{B(m_i - 1 + \alpha, n - m_i + 1 + \beta)}{B(\alpha, \beta)}}{Prob(0 < \widehat{C} \leq V | \alpha, \beta)}. \quad (7)$$

where $\{m_i: 0 < m_i \leq V\}_{i=0 \ldots M}$ is the vector of per-window counts (for the M windows with at least one matched segment and less than or equal to V counts), n is the population size, $\alpha$ and $\beta$ are the parameters for the beta function B, and Prob($0 < \widehat{C} \leq V | \alpha, \beta$) is the probability that a per-window count of matched segment is greater than zero and less than or equal to V conditional to $\alpha$ and $\beta$.

The probability distribution of C conditional to RGH is then given by:

$$Prob(\widehat{C=c} | RGH, V, c > 0) = \binom{n}{c} \frac{B(c+\alpha, n-c+\beta)}{B(\alpha, \beta)} / Prob(0 < \widehat{C} \leq V | \alpha, \beta), \quad (8)$$

wherein Prob($0 < \widehat{C} \leq V | \alpha, \beta$) represents a normalization factor that is a function of $\alpha$ and $\beta$ and given by:

$$Prob(0 < \widehat{C} \leq V | \alpha, \beta) = \sum_{c=1}^{V} \binom{n}{c} \frac{B(c+\alpha, n-c+\beta)}{B(\alpha, \beta)}. \quad (9)$$

In some embodiments, the method 100 uses maximum-likelihood estimation to determine the two parameters $\alpha$ and $\beta$ of the joint beta-binomial distribution $f(\{m_i\}|n,\alpha,\beta,V)$ using the same or similar optimization algorithms that are used in estimating Prob(C=c) as described above. In some embodiments, the method 100 uses the same or similar starting values for $\alpha$ and $\beta$ as are used to estimate Prob(C=c). Using the same starting values for the first and the second joint beta-binomial distribution minimizes the effect of the starting values on the differences between these two distributions.

II.C.3. Determine Pro$\widehat{b(RG\,H)}$ Estimate

In some embodiments, the method 100 then determines an estimate of Pro$\widehat{b(RG\,H)}$ based on Prob($\widehat{C}$=c) and Prob ($\widehat{C=c}$ |RGH). In some embodiments, Pro$\widehat{b(RG\,H)}$ is set to be maximum of $$\frac{1}{\frac{Prob(\widehat{C=c} | RGH)}{Prob(\widehat{C} = c)}},$$

which is equal to $$\frac{Prob(\widehat{C} = m)}{Prob(\widehat{C=m} | RGH)},$$

where m is the point at which $$\frac{Prob(\widehat{C=c} | RGH)}{Prob(\widehat{C} = c)}$$

is maximized. Thus, the method 100 only implicitly estimates Pro$\widehat{b(RG\,H)}$ by evaluating the ratio Prob($\widehat{C=c}$ |RGH)/Prob($\widehat{C}$=c). In some embodiments, the method 100 determines at least two estimates of Prob (RGH, V) based on the at least two Prob (C=c|RGH, V). In some embodiments, the method 100 determines two $\widehat{\text{Prob}}(\text{RGH}, V)$, estimates based on the two user-specified threshold values V, where each V are determined on two specified quantiles of all the counts in windows with at least one matched segment as described above. Determining the estimate of Prob(RGH) as a ratio of two probabilities ensures that the estimate as well as the corresponding weights fall with the range of zero to one, since the weight is also determined as a ratio of three probabilities that fall within the range of zero to one. The weight would be undefined, if Prob$(\widehat{C}=c)$ is zero. The above described estimation using a beta-binomial distribution ensures that any values of Prob $(\widehat{C}=c)$ are larger than zero.

II.C.4. Estimating Temporary Weights $\{w_c\}$ for Each Estimate of Prob(C=c|RGH)

The method 100 then determines temporary weights based on the estimates of Prob$(\widehat{C}=c)$, Prob$(\widehat{C=c}|\text{RGH})$, and $\widehat{\text{Prob}}(\text{RGH})$. These weights are temporary, since the method 100 uses these weights to determine the final weight for each window. The temporary weights can be represented by a vector $\{w_c\}_{c=0\ldots n}$ that is a series of values for different match counts and $w_c$ is the raw weight for a match count of c. Given the at least two estimates of Prob(C=c|RGH) in some embodiments, the method 100 determines temporary weights for each estimate of Prob(C=c|RGH) and then selects one series of temporary weights to determine the final weight.

If any optimization fails for one quantile it is ignored in the decision step, hence if temporary weights can only be estimated for one choice of quantile, then those temporary weights are the final weights. Considering multiple options for the quantile ensures that we are not missing a good weight vector to down weight purely because of the choice of a fixed quantile for all individuals. The choice of quantile for the estimation of Prob(C=c|RGH) is made for each individual by the observation which quantile most down weights the counts.

To determine the temporary weights, the method 100 initially determines raw weights $\{r_c\}_{c=0\ldots n}$ based on the estimates of Prob$(\widehat{C}=c)$, Prob$(\widehat{C=c}|\text{RGH})$, and $\widehat{\text{Prob}}(\text{RGH})$, wherein $r_c$ is the raw weight for a match count of c. In some embodiments, the initial values of raw weights $\{r_c\}_{c=0\ldots n}$ are determined by using equation 2. Subsequently, the method 100 determines the temporary weights from the raw weights so that the temporary weights satisfy the following three conditions:
1. the temporary weight of a window with one match in it has a weight of one, i.e. $w_{c=1}=1$;
2. the values of the temporary weights monotonically decreases with increasing match count c in a specific window, i.e. $w_c > w_{c+1}$ for all match counts c; and
3. the temporary weights default to one for all windows, if the estimates of Prob(C=c), Prob(C=c|RGH) or Prob (RGH) are poor.

In some embodiments, estimates of these probabilities are considered poor if the optimization algorithm used to determine the beta-binomial distributions fails, the number of per-window match counts falls below threshold value, e.g., 20, or the number of points used for fitting the beta-binomial distribution is below a minimum number.

The first two conditions can be met by enforcing that the weight monotonically decreases as the match count in a specific window increases. The rationale for a default weight of one is to avoid introducing more rather than removing noise in the TIMBER score calculation, since estimating probabilities of the weights based on underrepresented matched segment counts likely introduce noise in the calculation. Furthermore, since only low per-window match counts are measured in this case, the method 100 would take all matched segment counts, which are mainly low per-window match counts, into consideration without weighting down any particular matched segment counts. More specifically, the estimation the probabilities using the beta-binomial distributions is limited when interpreting low match count levels.

In some embodiments, the temporary weights $\{\tilde{w}_c\}_{c=0\ldots n}$ are determined by the following two steps that are consistent with the first two above conditions, i.e. the first temporary weight equaling one and the temporary weights monotonically decreasing with increasing match count. In the first step, the method 100 sets the temporary weights to one for all windows with a match count less than or equal to M, wherein M is the count for which the ratio between the two beta-binomial estimated distributions is highest. In the second step, after the count for which Prob(RGH) was "estimated," any increase in the weight with respect to increased match count is changed to be a zero increase. In some embodiments, the method 100 performs the two steps for all c by applying the following algorithm (except when applying the default weight because of poor probability estimates):

$$1.\ \tilde{w}_c = 1, \quad \text{if } c \leq M, \tag{10}$$

$$2.\ d_c = \begin{cases} 0, & \text{if } r_c > r_{c-1} \\ r_c - r_{c-1}, & \text{else} \end{cases}, \tag{11}$$

$$\tilde{w}_c = 1 + \sum_{i=M+1}^{c} d_i, \quad \text{if } c > M. \tag{12}$$

Figure 6:
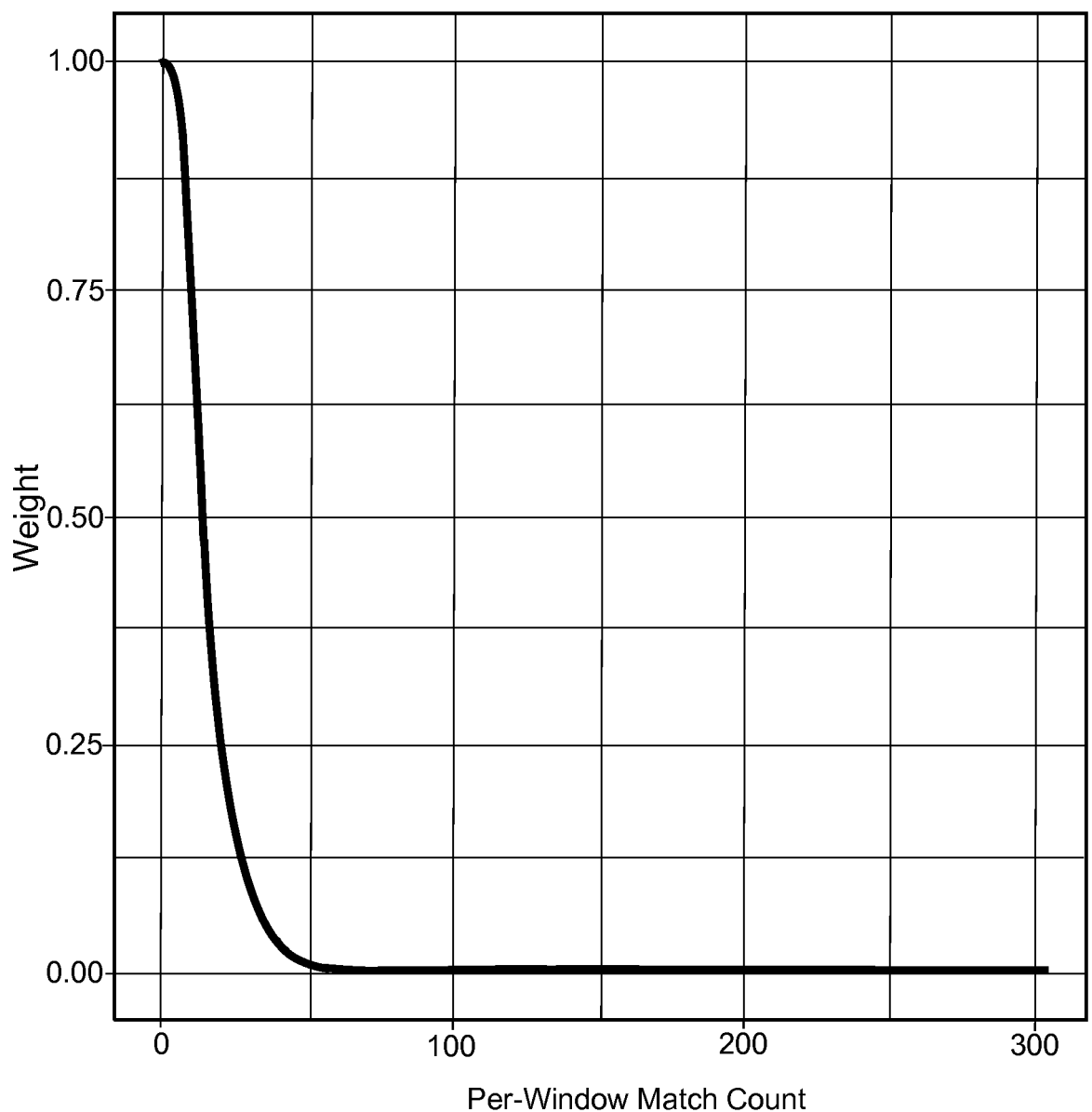
FIG. 6 is an example of the estimated per-window weight (in the y-axis) as a function of the possible per-window match count (in the x-axis), according to some embodiments.
Figure 7:
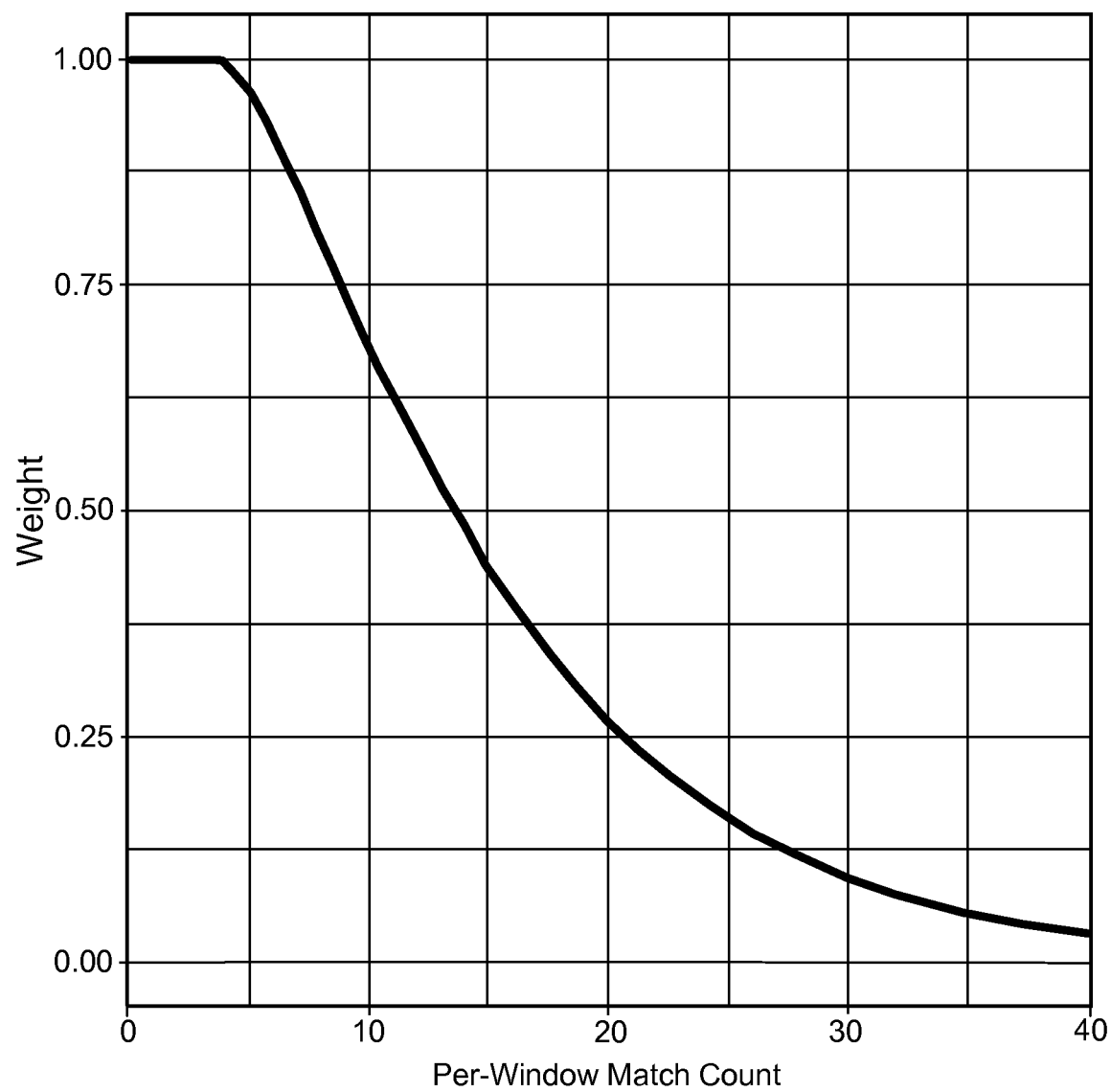
FIG. 7 is an example of the estimated per-window weight (in the y-axis) as a function of the possible per-window match count (in the x-axis), according to some embodiments.

FIGS. 6 and 7 illustrate an example of the per-window temporary weights $\{w_c\}$ (y-axis) as a function of the possible per-window match count c (x-axis). In particular, FIG. 7 shows more detail than FIG. 6, since the maximum value of the per-window match count c displayed along the x-axis is set to 40. In this example, M is 4.

II.C.5. Estimating the Final Weights $\{w_i\}$

The method 100 includes determining final weights $\{w_i\}_{i=1\ldots K}$ for weighting all matched segment windows based on the temporary weights $\{\tilde{w}_{c,V}\}_{c=0\ldots c_{max},V}$. In some embodiments, the final weight $w_i$ is the temporary weights for a given estimate of Prob(C=c|RGH,V), i.e. a given V, which minimizes the sum of the weighted per-window segment count:

$$\{\overline{w}_c\}_{c=0\ldots c_{max}} = \underset{\{w_{c,V}\}_V}{\operatorname{argmin}} \sum_{i=1}^{K} k_i \cdot \tilde{w}_{c=k_i,V}, \tag{13}$$

$$\{w_i\}_{i=1\ldots K} = \{w_i : w_i = \overline{w}_{k_i}, i = 1 \ldots K\}. \tag{14}$$

Figure 8:
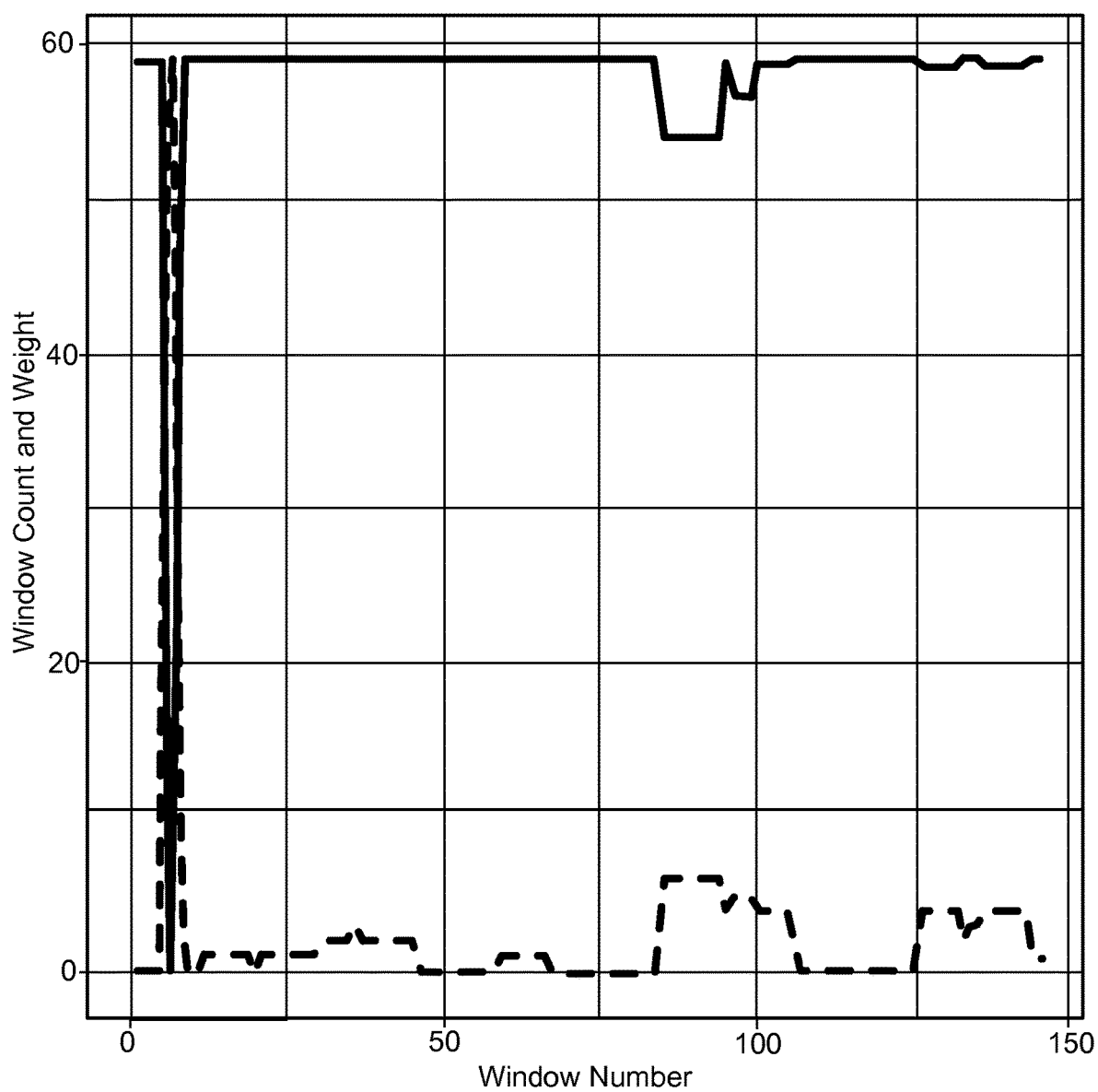
FIG. 8 illustrates an example for the weights (solid line) given the per-window counts (dashed line) from the original example in FIG. 1, according to some embodiments.

In summary, given the estimates for specific parameters for Prob(C=c), multiple estimates of Prob (C=c|RGH), Prob (RGH) and some post-processing, we can find the weight for a given window in a given individual i. FIG. 8 illustrates an example for the weights (solid line) given the per-window counts from the original example in FIG. 2 (dashed line). For comparative purposes only, the weight is re-scaled so that a weight of 1 has a value of 59 according to the y-axis. The weight calculation generates for every individual a weight value (within the interval 0 and 1) for the K segment windows.

II.D. Calculate Weighted Sum of Per-Window cM Widths $cM_2^{A,B}$

The method 100 includes calculating 112 a weighted sum of per-window cM widths for each matched segment based on the first cM width and the weights associated with the segment windows of the matched segment, according to some embodiments. In particular, the method calculates the weighted sum of per-window cM widths for a matched segment, between person A and person B, given the individual-specific window estimated weights for person A and person B. The weighted sum of per-window cM widths $cM_2^{A,B}$ is the sum of the first cM widths $cM_{1,i}$ for each window i that the matched segment spans weighted by the product of the weights for both individuals, A and B, in those segment windows:

$$cM_2^{A,B} = \sum_{i=WIN_{start}}^{WIN_{end} \leq K} w_i^A \cdot w_i^B \cdot cM_{1,i}, \quad (15)$$

for a segment between individuals A and B, starting at window $WIN_{start}$ and ending at window $WIN_{end}$ with $w_{win}^A$ and $w_{win}^B$ being the weights for both individuals, respectively, in window i. If the windows are either the start or the end window of the matched segment, the window widths are updated to be from either the first genetic marker in the window or to the last genetic marker in the window, respectively.

Figure 9:
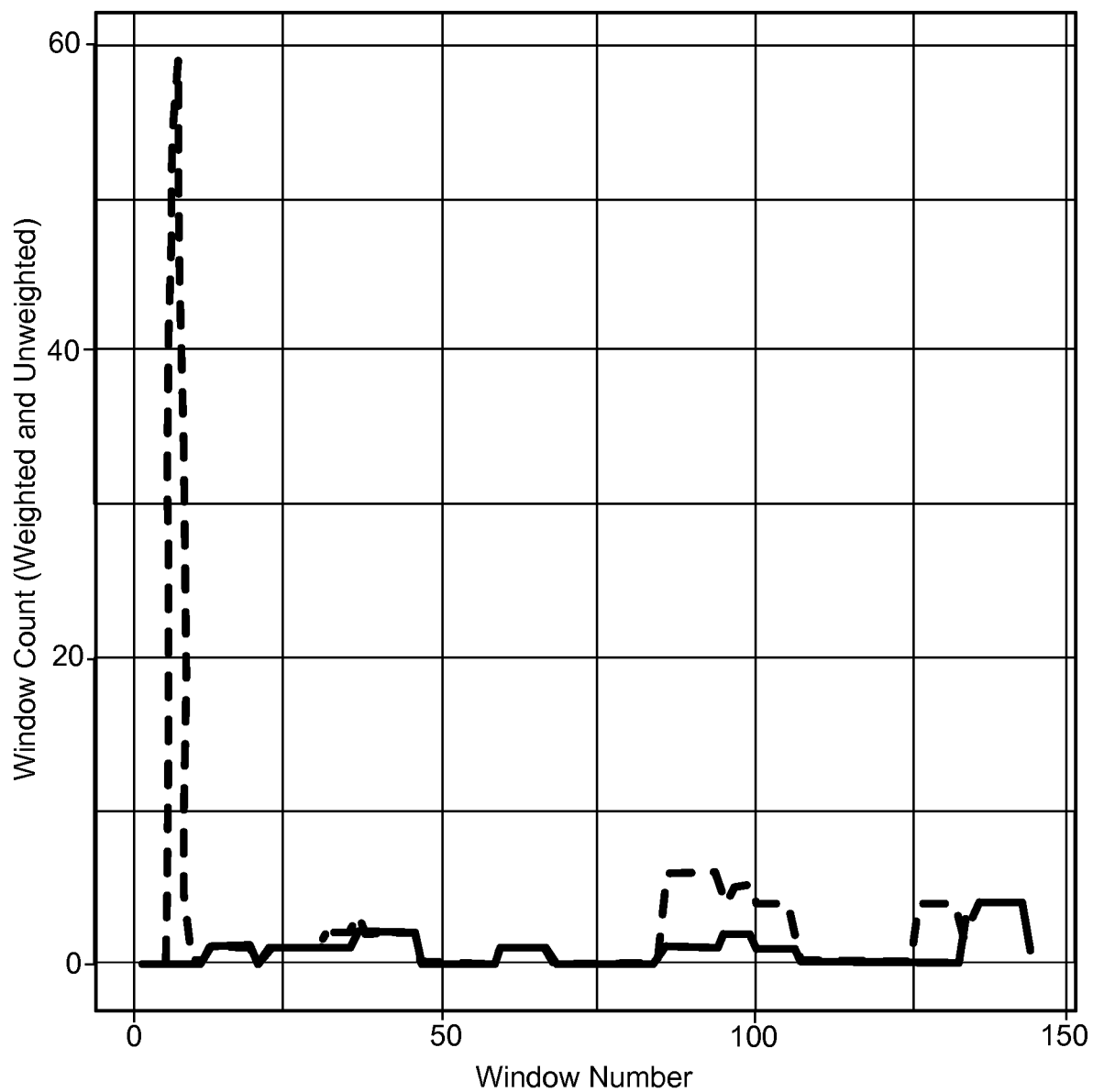
FIG. 9 is an example of per-window match counts on a chunk of the genome for one individual both pre-TIMBER (dashed line) and post-TIMBER (solid line), according to some embodiments.

The weights are in the interval between 0 and 1 and can intuitively be thought of as a probability that this window should contribute to the new "width". Taking the product of the weights for individuals A and B ensures that the window is valid in both individuals to be able to contribute to the weighted sum of per-window cM widths. The first and weighted sum of per-window cM widths would be identical, if all weights are equal to one. The new "width" or weighted sum of per-window cM widths typically is smaller than the raw or first cM width, and, therefore, down weights those matches in windows where there are a high number of matches either in individual A or individual B for a large population. Thus, the down weighting results in downweight matches, which are less likely to be from recent genealogical history of the individuals. FIG. 9 illustrates an example of per-window match counts on a chunk of the genome for one individual both pre-TIMBER (dashed line) and post-TIMBER (solid line).

III. Ancestral Relationship Prediction

The method 100 includes estimating 114 a degree of ancestral relatedness between two individuals based on the weighted sum of per-window cM widths of each matched segment between the two individuals, according to some embodiments. If a pair of individuals have a total sum of first cM widths of less than 60 cM, which effectively removes close relatives from the relatedness evaluation, the relationship distance is predicted based on the sum of all the weighted sum of per-window cM widths of the shared segments. Otherwise, the summation of the first cM widths is used. This results in a relationship prediction that is more accurate for more distant relationships, while being as accurate for close relationships. This especially true for certain ethnic groups (for example Jewish people) and whether they are assigned to be distantly related or not.

The method 100 by using, for example, the degree of ancestral relatedness, allows people to find their recent relatives and provide them with new information about their genealogy within a network of relatives (with known genealogy). In some embodiments, the degree of relatedness between two individuals represents a probability that the two individuals are ancestrally related and is equal to the weighted sum of per-window cM widths of the individuals' matched segments. In some embodiments, the degree of relatedness between two individuals is a binary yes or no answer whether the two individuals are ancestrally related based on the weighted sum of per-window cM widths. For example, if the weighted sum of per-window cM widths exceeds a relatedness threshold value, the two individuals are said to be ancestrally related. In some embodiments, the relatedness threshold value is 20, 25, 30, 35, 40, 45, 50 cM, or any value larger than 20 cM. In some embodiments, the relatedness threshold value is 30, 40 or 50 cM.

Previously, the prediction of the distance of relationship between two individuals (e.g. cousins, third cousins, etc.) was based purely on the total width of all IBD segments, where the width of the IBD segment was determined by its width in recombination distance (in cM). In this method 100, a total score is calculated based on all IBD segments between two individuals to provide relationship distance. However, method 100 uses a sum of reweighted weighted sum of per-window cM widths in this calculation to predict relatedness, if the sum of first cM widths of less than 60 cM.

In one examples, weight profiles are generated from matches to a static reference set of just over 300K samples. Those weights are then used to re-score, i.e., re-weight, all matches between any pair of individuals in the database. The weights used by method 100 are stored in their own database. In one example embodiment, based on the analysis of test sets and real data, a threshold cM width of 5 cM was the minimum width, at which a matched segment is included in the weight estimation 110 and weighted sum of per-window cM widths calculation 112.

IV. Example

In an example, TIMBER behavior was analyzed with a simulated test set. The test set consisted of exactly 3703 pairs of genotypes (7406 individual samples) representing relationships from parent/child (1 meiosis) to 5th cousins (12 meioses) and all in-between. Each relationship was created independently of all others by simulating meioses to create genotypes that represent individuals in the relevant part of the pedigree. The "founders" from which non-simulated genotypes come were a set of approximately 24,000 genotypes from the database that have no close estimated relationships among them based on the analysis of the non-weighted first cM widths. "Founders" used to create a given relationship were discarded and not used at all for simulating any of the other relationships. The fact that the initial founders had very few genuine relationships and were not reused helped to minimize the likelihood of relationships among synthetic genotypes that we were unable to document, but that were still possible. The test set might not be ideal for a real world scenario, since individuals were randomly paired to be parents. However, since in the simulation the real RGH segments were known, the simulation provided a way to verify how well TIMBER helped refining the analysis of matched segments. In the test, just over 300 pairs of each meiosis level were represented between from parent-child relationships (1 meiosis) to 5th cousins (12 meioses).

TABLE 1

TIMBER results for different minimum cutoffs (=threshold cM width)

| Segment | Percentage of matched segments kept | | |
|---|---|---|---|
| | Min. of 5 cM | Min. of 6 cM | Min. of 7 cM |
| True | 92 | 88 | 84 |
| False | 3 | 1 | 1 |

Table 1 illustrates that TIMBER kept the vast majority (around 90%) of initially discovered IBD segments that overlap with real IBD segments. The results did not largely vary with respect to different first cM widths of 5, 6 and 7 and were used to determine if a discovered IBD segment was retained or not. TIMBER only kept at most 3% of the initially discovered IBD segments that are false positives. Thus, TIMBER presents a very useful filter for keeping the real signals while removing the false positive signals of IBD segments between pairs of individuals due to the individuals' recent genealogical history. No "ibs" filtering was used to filter the raw and non-weighted output of matched IBD segments.

Figure 10:
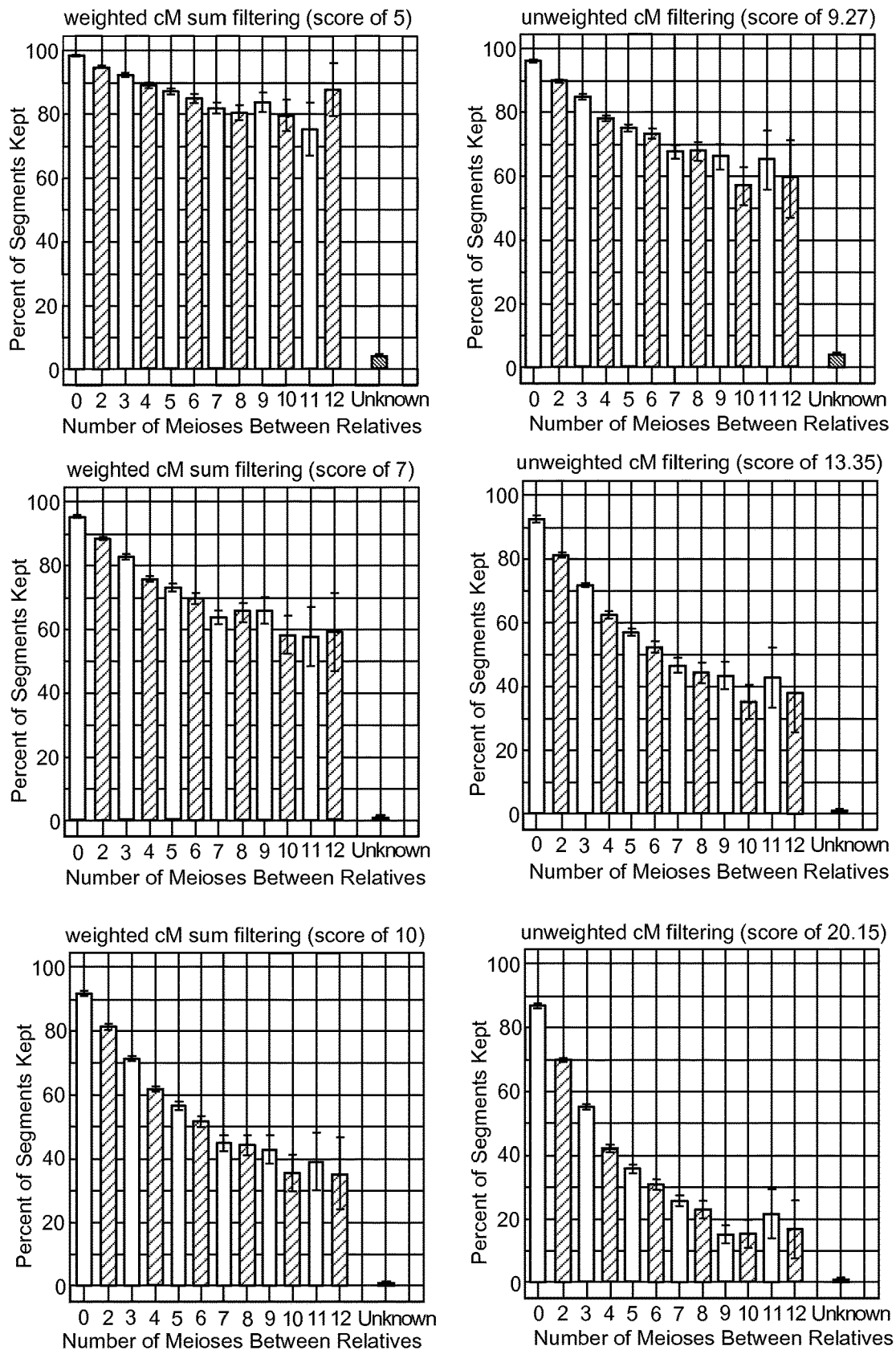
FIG. 10 illustrates results from TIMBER using different unweighted cM width scores, i.e., first cM width filters, and weighted cM sum scores, including the matched percentages of segments kept for the known and unknown meiosis, according to some embodiments.

Table 2 shows that TIMBER was slightly more accurate for closer relatives, but generally worked well across the spectrum of recent genealogical history from parent-child relationships (1 meiosis) to 5th cousins (12 meioses). FIG. 10 illustrates results from TIMBER using different raw cM width, i.e., first cM width filters, including the matched percentages of segments kept for the known and unknown meioses.

TABLE 2

TIMBER results for true segments by meiosis and different minimum cutoffs

| Meiosis | Percentage of matched segments kept | | |
|---|---|---|---|
| | Min. of 5 cM | Min. of 6 cM | Min. of 7 cM |
| 1 | 98 | 97 | 95 |
| 2 | 95 | 91 | 89 |
| 3 | 92 | 87 | 83 |
| 4 | 88 | 82 | 76 |
| 5 | 87 | 80 | 73 |
| 6 | 85 | 76 | 69 |
| 7 | 82 | 72 | 64 |
| 8 | 81 | 74 | 65 |
| 9 | 84 | 73 | 66 |
| 10 | 80 | 69 | 58 |
| 11 | 75 | 68 | 57 |
| 12 | 88 | 71 | 59 |

V. Additional Considerations

Computing system 120 is implemented using one or more computers having one or more processors executing application code to perform the steps described herein, and data may be stored on any conventional non-transitory storage medium and, where appropriate, include a conventional database server implementation. For purposes of clarity and because they are well known to those of skill in the art, various components of a computer system, for example, processors, memory, input devices, network devices and the like are not shown in FIG. 1B. In some embodiments, a distributed computing architecture is used to implement the described features. One example of such a distributed computing platform is the Apache HADOOP® project available from the Apache Software Foundation.

In addition to the embodiments specifically described above, those of skill in the art will appreciate that the invention may additionally be practiced in other embodiments. Within this written description, the particular naming of the components, capitalization of terms, the attributes, data structures, or any other programming or structural aspect is not mandatory or significant unless otherwise noted, and the mechanisms that implement the described invention or its features may have different names, formats, or protocols. Further, the system may be implemented via a combination of hardware and software, as described, or entirely in hardware elements. Also, the particular division of functionality between the various system components described here is not mandatory; functions performed by a single module or system component may instead be performed by multiple components, and functions performed by multiple components may instead be performed by a single component. Likewise, the order in which method steps are performed is not mandatory unless otherwise noted or logically required. It should be noted that the process steps and instructions of the present invention could be embodied in software, firmware or hardware, and when embodied in software, could be downloaded to reside on and be operated from different platforms used by real time network operating systems.

Algorithmic descriptions and representations included in this description are understood to be implemented by computer programs. Furthermore, it has also proven convenient at times, to refer to these arrangements of operations as modules or code devices, without loss of generality.

Unless otherwise indicated, discussions utilizing terms such as "selecting" or "computing" or "determining" or the like refer to the action and processes of a computer system, or similar electronic computing device, that manipulates and transforms data represented as physical (electronic) quantities within the computer system memories or registers or other such information storage, transmission or display devices.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a non-transitory computer readable storage medium, such as, but is not limited to, any type of disk including floppy disks, optical disks, DVDs, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented are not inherently related to any particular computer or other apparatus. Various general-purpose systems may also be used with programs in accordance with the teachings above, or it may prove convenient to construct more specialized apparatus to perform the required method steps. The required structure for a variety of these systems will appear from the description above. In addition, a variety of programming languages may be used to implement the teachings above.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

What is claimed is:

1. A computer program product for estimating a degree of ancestral relatedness between two individuals, the computer program product stored on a non-transitory computer readable medium and including instructions configured to cause a processor to execute steps comprising:
   receiving haplotype data for a population of individuals, the haplotype data including a plurality of genetic markers shared among the individuals;
   dividing the haplotype data into segment windows based on the genetic markers;
   for each individual in the population:
      based on the genetic markers, matching segments of the haplotype data that are identical between the individual and any other individual in the population, each matched segment having a first cM width exceeding a threshold cM width and being part of one or more of the segment windows;
      counting the matched segments in each segment window;
      estimating a weight associated with each segment window based on the count of matched segments in the associated segment window;
      calculating a weighted sum of per-window cM widths for each matched segment based on the first cM width and the weights associated with the segment windows of the matched segment; and
      estimating a degree of ancestral relatedness between two individuals based on the weighted sum of per-window cM widths of each matched segment between the two individuals.

2. The computer program product of claim 1, wherein threshold cM width is 5 cM, 6 cM, 7 cM, 8 cM, 9 cM, 10 cM, or any real number within the range of 5 cM to 10 cM.

3. The computer program product of claim 1, wherein the weight associated with each segment window decreases if the count of matched segments in the associated segment window increases.

4. The computer program product of claim 1, wherein two individuals are closely related if the sum of the first cM widths of matched segments over all matched segments between the two individuals exceeds a pre-defined close relative threshold value of 30, 40, 50, 60, 70, 80, 90, 100 cM or any value from the range of 30 to 200 cM.

5. The computer program product of claim 1, wherein a size of the segment windows comprises 50, 60, 70, 80, 90, 100, 110, 120, 130, 140, 150 genetic markers or any number that falls within the range of 50 to 500 genetic marker.

6. The computer program product of claim 1, wherein a size of the population is larger than 300,000.

7. The computer program product of claim 1, wherein for a population size n and a number of genetic markers per segment window d a number of segment windows K is approximated as:

$$K = n/d.$$

8. The computer program product of claim 1, wherein close relatives are removed from the population.

9. The computer program product of claim 8, wherein close relatives comprise two individuals having a total first cM width larger than 60 cM.

10. The computer program product of claim 1, wherein the degree of relatedness between two individuals comprises a probability that the two individuals are ancestrally related.

11. The computer program product of claim 1, wherein the degree of relatedness between two individuals comprises a binary yes or no answer whether the two individuals are ancestrally related.

12. The computer program product of claim 1, wherein the weight associated with a segment window for individual A is approximated as:

$$w_i^A = \frac{Prob(\widehat{C = k_i} \mid RGH) \operatorname{Prob}(\widehat{RGH})}{\operatorname{Prob}(\widehat{C} = k_i)},$$

wherein $\operatorname{Prob}(\widehat{C = c} \mid RGH)$, $\operatorname{Prob}(\widehat{RG\,GH})$, $\operatorname{Prob}(\widehat{C} = c)$ are the estimates of a probability of an RGH segment given a measured count c of matched segments in a window, a probability of an RGH segment in a window, and the probability of measuring a count c of matched segments in a window, respectively.

13. The computer program product of claim 1, wherein weighted sum of per-window cM widths for a segment between two individuals A and B is calculated as:

$$cM_2^{A,B} = \sum_{i=WIN_{start}}^{WIN_{end} \leq K} w_i^A \cdot w_i^A \cdot cM_{1,i},$$

wherein $cM_{1,i}$ is the first cM width for each window i that the matched segment spans and the segment between individuals A and B starts at window $WIN_{start}$ and ends at window $WIN_{end}$ with $w_i^A$ and $w_i^B$ being the weights associated with segment window i for individual A and B, respectively.

14. The computer program product of claim 1, wherein estimating the weight comprises calculating temporary weights $\tilde{w}_c$ for the count c of matched segments in the associated segment window is approximated as:

$$\tilde{w}_c = 1, \text{ if } c \leq M,$$

$$d_c = \begin{cases} 0, & \text{if } r_c > r_{c-1} \\ r_c - r_{c-1}, & \text{else} \end{cases},$$

$$\tilde{w}_c = 1 + \sum_{i=M+1}^{c} d_i, \text{ if } c > M,$$

wherein $r_c$ is the weight based on the count of matched segments c and approximated as:

$$r_c = \frac{\mathrm{Prob}(\widehat{C=c} \mid RGH)\mathrm{Prob}(\widehat{RGH})}{\mathrm{Prob}(\widehat{C}=c)}.$$

15. The computer program product of claim 12, wherein the Prob ($\widehat{C=c}$ |RGH) is based on a user specified threshold value V, and Prob ($\widehat{C=c}$ |RGH,V) is approximated as:

$$\mathrm{Prob}(\widehat{C=c} \mid RGH, V, c > 0) = \binom{n}{c}\frac{B(c+\alpha, n-c+\beta)}{B(\alpha, \beta)} \Big/ \mathrm{Prob}(0 < \widehat{C} \leq V \mid \alpha, \beta),$$

wherein n is the size of the population, α, β are parameters of the Beta function B.

16. The computer program product of claim 15, wherein a and is estimated by using a maximum likelihood estimation of a joint distribution approximated as:

$$f(\{m_i\} \mid n, \alpha, \beta, V, m_i > 0) = \frac{\prod_{i=1}^{M}\binom{n}{m_i-1}\frac{B(m_i-1+\alpha, n-m_i+1+\beta)}{B(\alpha, \beta)}}{\mathrm{Prob}(0 < \widehat{C} \leq V \mid \alpha, \beta)}.$$

17. The computer program product of claim 12, wherein Prob($\widehat{RGH}$) is approximated by the maximum of:

$$\frac{1}{\frac{\mathrm{Prob}(\widehat{C=c} \mid RGH)}{\mathrm{Prob}(\widehat{C}=c)}}.$$

18. The computer program product of claim 12, wherein Prob($\widehat{C}$ =c) is approximated as:

$$\mathrm{Prob}(\widehat{C} = c \mid c > 0) = \binom{n}{c}\frac{B(c+\alpha, n-c+\beta)}{B(\alpha, \beta)},$$

wherein n is a size of the population and α, β are parameters of the Beta function B.

19. The computer program product of claim 18, wherein α and β is estimated by using a maximum likelihood estimation of a joint distribution approximated as:

$$f(\{k_i\} \mid n, \alpha, \beta, k_i > 0) = \prod_{i=1}^{K}\binom{n}{k_i-1}\frac{B(k_i-1+\alpha, n-k_i+1+\beta)}{B(\alpha, \beta)}.$$

20. The computer program product of claim 15, wherein the user specified threshold value V may include two specified quantiles, a first specified quantile equal to 50%, 55%, 60%, 65%, 70%, or 75% and a second specified quantile equal to 75%, 80%, 85%, or 90%, to determine at least two estimates of Prob(C=c|RGH,V).

* * * * *

UNITED STATES PATENT AND TRADEMARK OFFICE
CERTIFICATE OF CORRECTION

PATENT NO.         : 10,720,229 B2
APPLICATION NO.    : 15/519104
DATED              : July 21, 2020
INVENTOR(S)        : Barber et al.

Page 1 of 1

It is certified that error appears in the above-identified patent and that said Letters Patent is hereby corrected as shown below:

On the Title Page

Item (72), Column 1, in "Inventors", Line 1, after "Mathew" delete "J" and insert -- J. --, therefor.

In the Claims

In Column 22, in Claim 7, Line 3, delete "d a number" and insert -- d, a number --, therefor.

In Column 22, in Claim 12, Line 30, delete "Prob(RG GH)," and insert --Prob(RGH),--, therefor.

In Column 22, in Claim 13, Lines 41-43, delete "$w^A_i \cdot w^A_i \cdot cM_{1,i}$," and insert -- $w^A_i \cdot w^B_i \cdot cM_{1,i}$ --, therefor.

In Column 22, in Claim 13, Line 50, delete "individual" and insert -- individuals --, therefor.

In Column 23, in Claim 15, Line 18, delete "is the size" and insert -- is a size --, therefor.

In Column 23, in Claim 16, Line 21, delete "a and" and insert -- α and β --, therefor.

In Column 23, in Claim 17, Line 33, delete "Prob(RG GH)" and insert --Prob(RGH)--, therefor.

Signed and Sealed this
Twenty-ninth Day of December, 2020

Andrei Iancu
*Director of the United States Patent and Trademark Office*